US010245355B2

(12) United States Patent
Ingber et al.

(10) Patent No.: US 10,245,355 B2
(45) Date of Patent: Apr. 2, 2019

(54) MODIFICATION OF SURFACES FOR FLUID AND SOLID REPELLENCY

(71) Applicant: President and Fellows of Harvard College, Cambridge, MA (US)

(72) Inventors: Donald Ingber, Boston, MA (US); Daniel C. Leslie, Brookline, MA (US); Michael Super, Lexington, MA (US); Alexander L. Watters, Melrose, MA (US); Anna Waterhouse, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 321 days.

(21) Appl. No.: 14/904,399

(22) PCT Filed: Jul. 10, 2014

(86) PCT No.: PCT/US2014/046225
§ 371 (c)(1),
(2) Date: Jan. 11, 2016

(87) PCT Pub. No.: WO2015/053834
PCT Pub. Date: Apr. 16, 2015

(65) Prior Publication Data
US 2016/0144079 A1 May 26, 2016

Related U.S. Application Data

(60) Provisional application No. 61/844,636, filed on Jul. 10, 2013.

(51) Int. Cl.
*B05D 5/08* (2006.01)
*B05D 5/12* (2006.01)
(Continued)

(52) U.S. Cl.
CPC ............... *A61L 31/08* (2013.01); *A61L 27/34* (2013.01); *A61L 29/08* (2013.01); *A61L 29/085* (2013.01);
(Continued)

(58) Field of Classification Search
USPC ......... 428/447, 36.1, 36.91, 424.4; 427/384; 523/213; 106/2
See application file for complete search history.

(56) References Cited

U.S. PATENT DOCUMENTS 4,876,126 A * 10/1989 Takemura ............. A61L 29/085
427/2.1
5,578,340 A * 11/1996 Ogawa ................. A61L 33/0088
427/2.1
(Continued)

FOREIGN PATENT DOCUMENTS

EP 0166998 A2 1/1986
EP 0675953 B1 1/2009
(Continued)

OTHER PUBLICATIONS

Wong et al., "Bioinspired Self-Repairing Slippery Surfaces with Pressure-Stable Omniphobicity", Nature, vol. 477, No. 7365, pp. 443-447, Sep. 22, 2011.
(Continued)

*Primary Examiner* — Tae H Yoon
(74) *Attorney, Agent, or Firm* — Wilmer Cutler Pickering Hale and Dorr LLP

(57) ABSTRACT

Articles, methods of making, and uses for modifying surfaces for liquid repellency are disclosed. The liquid repellant surfaces comprise a surface comprising an anchoring layer. The anchoring layer, which forms an immobilized molecular anchoring layer on the surface, has anchoring molecules, where each anchoring molecule has a head group that is
(Continued)

covalently linked to the surface and a functional tail group. The anchoring molecules are crosslinked to each other to form a crosslinked network. The functional tail group has an affinity for a lubricating liquid, which is applied to the treated surface to form a lubricating layer. The anchoring layer and replenishable lubricating liquid are held together by non-covalent attractive forces. Together, these layers form an ultra-repellant slippery surface that repels certain immiscible liquids and prevents adsorption, coagulation, and surface fouling by components contained within.

41 Claims, 10 Drawing Sheets

(51) Int. Cl.
| | |
|---|---|
| A61L 27/34 | (2006.01) |
| A61L 29/14 | (2006.01) |
| A61L 31/10 | (2006.01) |
| A61L 33/00 | (2006.01) |
| A61L 31/08 | (2006.01) |
| A61L 29/08 | (2006.01) |
| C09D 5/16 | (2006.01) |
| A61L 31/14 | (2006.01) |

(52) U.S. Cl.
CPC ............... *C09D 5/16* (2013.01); *A61L 31/14* (2013.01); *A61L 2400/10* (2013.01); *A61L 2420/02* (2013.01); *B05D 5/08* (2013.01); *B05D 5/086* (2013.01)

(56) References Cited

U.S. PATENT DOCUMENTS

| | | | | |
|---|---|---|---|---|
| 6,017,577 | A * | 1/2000 | Hostettler | A61L 29/085 427/2.12 |
| 8,425,459 | B2 | 4/2013 | Wang | |
| 2006/0147492 | A1* | 7/2006 | Hunter | A61B 17/11 424/426 |
| 2007/0166344 | A1 | 7/2007 | Qu et al. | |
| 2008/0171836 | A1* | 7/2008 | Lee | C08G 65/33389 525/418 |
| 2010/0145286 | A1* | 6/2010 | Zhang | A61L 17/005 604/265 |
| 2010/0184913 | A1 | 7/2010 | Ebbrecht et al. | |

FOREIGN PATENT DOCUMENTS

| | | |
|---|---|---|
| WO | WO-93/17077 A1 | 9/1993 |
| WO | WO-02/15955 A2 | 2/2002 |
| WO | WO-2012/135834 A2 | 10/2012 |

OTHER PUBLICATIONS

European Search Report dated Feb. 2, 2017, in Application No. 14852476.2, 9 pages.

International Search Report dated Mar. 24, 2015, for International Application No. PCT/US2014/046225 filed Jul. 10, 2014 published on Apr. 16, 2015 as International Publication No. Wo 2015-053834, 3 pp.

Written Opinion of the International Searhcing Authority dated Mar. 24, 2015, for International Application No. PCT/US2014/046225 filed Jul. 10, 2014 published on Apr. 16, 2015 as International Publication No. WO 2015-053834, 12 pages.

Tuteja, A et al. Robust omniphobic surfaces. PNAS, vol. 105, No. 47, Nov. 25, 2008, pp. 18200-18205 [online], [retrieved on 2015-D2-26). Retrieved from the Internet <URL:http://www.pnas.org/content/105/47/18200.full.pdf+html>; abstract; p. 18200, col. 2, paragraph 2; p. 18201, col. 1, paragraph 1, p. 18201, figure 1A; p. 18202, col. 2, paragraph 1; .p. 18203, col. 2, paragraphs 3-5.

Marzano, A. Clinical Impact of AlH1/N1/09 Influenza in Patients with Cirrhosis: Experience from a Nosocomial Cluster of Infection. Journal of Medical Virology. vol. 85, Jan. 2013, pp. 1-7 [online), [retrieved on Feb. 26, 2015). Retrieved from the Internet <URL: http://onlinelibrary.wiley.com/doi/1 0. 1 002/jmv .23454/abstract;jsessionid=DOEFD1FOCOE39A23915024181624D368. f04t02>; p. 1, col. 2, paragraph 1.

Hamrock, BJ. Fundamentals of Fluid Film Lubrication. NASA Scientific and Technical Information Program, 1991 [online]. [retrieved on Feb. 26, 2015]. Retrieved from the Internet <URL: http:l/ntrs.nasa.gov/archive/nasa/casi.ntrs.nasa.gov/1991 0021217 .pdf>; p. 12, paragraph 3.

Merkel, Ret ai: Molecular Friction and Epitactic Coupling Between Monolayers in Supported Bilayers. Journal de Physique, vol. 50, No. 12, 1989, pp. 1535-1555 [online). [retrieved on Feb. 26, 2015). Retrieved from the Internet <URL:: https://hal.archives-ouvertes.fr/jpa-00211 013/document>; p. 1538, paragraph 3; p. 1541, figure 2.

Ma, X et al. Spreading of PFPE Lubricants on Carbon Surfaces: Effect of Hydrogen and Nitrogen Content. Tribology Letters, vol. 6, No, 1, Jan. 1999, pp. 9-14 (online), (retrieved on Feb. 26, 2015]. Retrieved from the Internet <URL: http://www .researchgate.net/profile/Bruno_Marchon/publication/226093501_ Spreading_ of PFPE_ lubricants_on_carocin_surfaces_effect_of hydrogen_and_nitrogen_ content/links/Odeec529670284fd9fOOOOOO.pdf>; p. 9, col. 1, paragraph 1.

* cited by examiner

MODIFICATION OF SURFACES FOR FLUID AND SOLID REPELLENCY

CROSS-REFERENCE TO RELATED APPLICATIONS

This application is a 371 U.S. National Stage Application, which claims the benefit of International Application No.: PCT/US2014/046225, having an International Filing Date of Jul. 10, 2014, which claims the benefit of the earlier filing date of U.S. Patent Application No. 61/844,636, filed on Jul. 10, 2013, the contents of which are hereby incorporated by reference in their entirety.

STATEMENT CONCERNING GOVERNMENT RIGHTS IN FEDERALLY-SPONSORED RESEARCH

This invention was made with government support under Grant No. N66001-11-1-4180 awarded by U.S. Department of Defense/DARPA. The government has certain rights in this invention.

TECHNICAL FIELD

The present application relates to articles that have been modified to provide slippery surfaces. More particularly, the present application relates to articles for use in biological and food container environments that have been modified to provide slippery surfaces.

BRIEF DESCRIPTION OF THE DRAWINGS

The following figures are provided for the purpose of illustration only and are not intended to be limiting.

DETAILED DESCRIPTION

Figure 1:
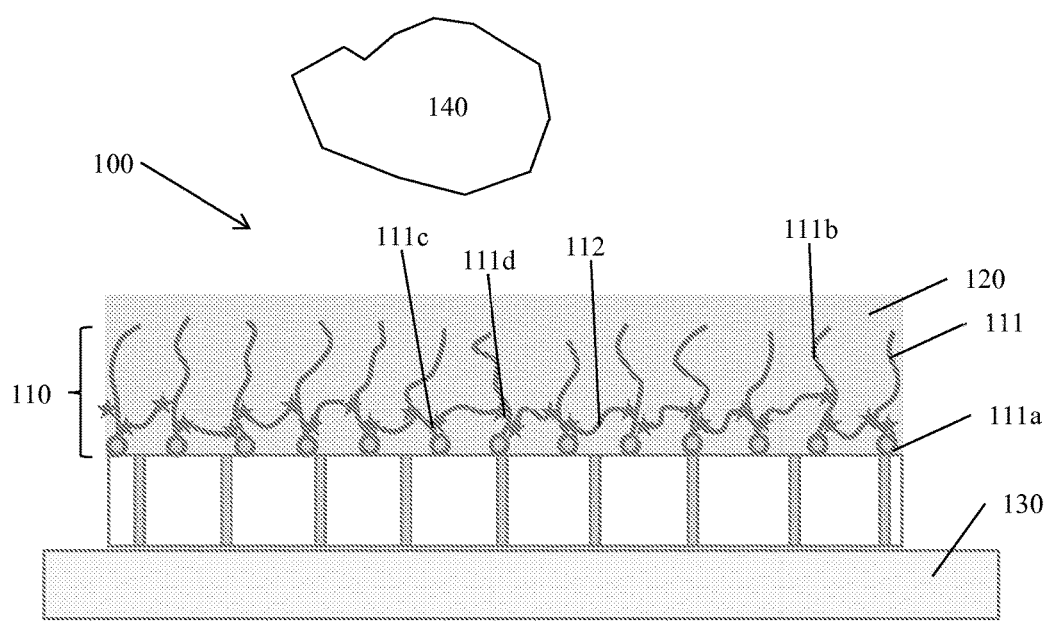
FIG. 1 is a schematic of a slippery liquid immobilized coating surface in accordance with the present disclosure, in which an anchoring layer of crosslinked immobilized molecules that exhibit chemical properties necessary to interact with and retain a lubricating layer of a lubricating liquid molecules that are immiscible with a repellent material in accordance with certain embodiments.

Methods for making most solid surfaces ultra-repellant to liquids, molecules or particulates contained within liquids, and dry solids are described. Further, methods for reducing adhesion and friction between two solid surfaces are provided.

U.S. Patent Application Nos. 61/585,059, filed on Jan. 10, 2012, U.S. Provisional Patent Application No. 61/692,079, filed Aug. 22, 2012, and Patent Cooperation Treaty Application No. PCT/US13/21056, filed on Jan. 10, 2013, all of which are hereby incorporated by reference in their entirety, describe the formation of an article having a slippery surface. The article has a substrate which has an anchoring layer. The anchoring layer has a head group attached to the substrate and a functional group directly or indirectly attached to the head group. The article further includes a lubricating layer that has a lubricating liquid having an affinity for the functional group and disposed over the anchoring layer, where the anchoring layer and the lubricating layer are held together by non-covalent attractive forces. The anchoring layer and the lubricating layer form a slippery surface configured and arranged for contact with a material that is immiscible with the lubricating liquid.

The present disclosure provides an improvement over such slippery surfaces described in U.S. Patent Application No. 61/585,059 by providing a slippery surface that is mechanically more robust and able to better retain the lubricating liquid. The present disclosure provides additional embodiments and advantages which will become apparent as discussed throughout the instant application.

The slippery liquid immobilized coating surfaces of the present disclosure are synthetic surfaces that include an anchoring layer secured to an underlying substrate that interacts with and retains a thin layer of a lubricating liquid. The anchoring layer includes anchoring molecules having head groups that interact preferentially with the underlying surface and present functional groups to the environment that have surface properties that interact favorably with the lubricating liquid. The anchoring molecules are arranged on the underlying surface to form an immobilized molecular anchoring layer on the surface. The anchoring layer further includes reactive components that crosslink the anchoring molecules together to form a crosslinked gel network. The lubricating layer forms at least a monomolecular layer over the anchoring layer, and the anchoring layer and the lubricating layer are held together by non-covalent attractive forces. The lubricating liquid has chemical affinity with the underlying gel network and is able to be retained by the gel network better than use of simple uncrosslinked anchoring molecules that are deposited over the substrate surface.

Certain embodiments of the present invention relate generally to surface coatings of a polymeric, glass, metallic, metal oxide, or composite substrate by organic ligands and mixtures of organic ligands and the uses of such chemically modified substrates for forming slippery surfaces by infusing a liquid lubricant onto a chemically functionalized substrate.

Certain embodiments of the present invention provide compositions of organic ligand and methods of forming coated substrates that offer control of surface energy, affinity, and compatibility with applied liquid lubricant, and improved stability and retention of such lubricant on the functionalized substrates.

The chemically functionalized substrates are useful when forming ultrasmooth, omni-repellent, self-healing, anti-coagulating, anti-biofouling and slippery surfaces by infusing lubricant onto the chemically functionalized surfaces. The compositions allow for tailoring of the type of the lubricants to be used as well as the type of foreign materials to be repelled or achieving long-term stability of retained lubricant in a variety of host media and shear conditions including liquids, gas, and solid hosts by changing the nature of the ligands.

An illustrative ultra-repellant surface 100 is shown in FIG. 1 (not drawn to scale). Referring to FIG. 1, an anchoring layer 110 of immobilized anchoring molecules 111 that exhibit chemical properties that bind and retain an ultra-thin lubricating layer 120 composed of a liquid is attached to a substrate 130. Substrate 130 can be a smooth or roughened surface. As shown, each anchoring molecule has a head group 111a that can bind to a substrate surface 130 and a functional tail group 111b directly or indirectly attached to the head group 111a. In certain embodiments, the head group 111a can provide a chemical linkage to the substrate 130, such as through covalent bonds. The tail group 111b can alter the surface properties of the substrate 130 to provide a desired property. For example, depending on the nature of the repellent material, the immobilized molecular anchoring layer 110 can increase the lipophobicity, hydrophobicity, or omniphobicity of the substrate surface 130. The tail groups 111b interact with the lubricating liquid (e.g., solubilized molecules of the lubricating liquid) that is applied to the treated surface. Thus, the tail groups 111b retain the molecules of the lubricating liquid by non-covalent attachment. The tail groups 111b and molecules of the lubricating liquid are arranged on the surface such that the molecules of lubricating liquid form a lubricating layer 120 on the surface. Because the affinity is based on the interaction of the lubricating liquid with the functional groups (e.g., tail groups 111b) of the anchoring layer, the lubricating layer can be very thin and can be about one molecular layer thick.

The anchoring layer 110 further includes additional crosslinking agents 112 that can react with two or more reactive groups 111c and 111d present on the anchoring molecules to form a crosslinked network. In certain embodiments, the crosslinking agents 112 can contain chemical groups that have an affinity with the lubricating liquid. In certain embodiments, a perfluorinated gel network is formed.

In certain embodiments, when utilized for medical, biological, or food container applications, any unreacted anchoring molecules 111 (e.g., not bound to the underlying substrate 130 and/or the crosslinking agents 112), unreacted crosslinking agents 112, and reaction byproducts that can form are washed away. Particularly, when such unreacted anchoring molecules 111 (e.g., not bound to the underlying substrate 130 and/or the crosslinking agents 112), unreacted crosslinking agents 112, and reaction byproducts are harmful in the intended application, they must be washed away.

A lubricating liquid is then applied to the surface-modified substrate. The surface modifying anchoring layer enhances the wetting properties of the lubricating liquid and allows it to form a thin lubricating layer. The immobilized molecular anchoring layer allows the lubricating liquid to be added to smooth or roughened substrate 230 and still repel immiscible materials.

Repellent material 140 is the material to be repelled, and can be a liquid, particulate contained within a liquid, a complex fluid, a dry solid, or a solid surface. The selection of the lubricating liquid (and thus the composition of the underlying anchoring layer) is made to provide a lubricating layer in which the repellent material is immiscible.

The lubricating layer 120 is formed by immobilizing the anchoring layer 110 on the surface 100 and applying a lubricating liquid to the surface containing the immobilized monomolecular surface layer 110. The lubricating liquid wets the treated surface of the substrate and forms the lubricating layer 120. The anchoring layer 110 and lubricating layer 120 are held together by non-covalent attractive forces. Together, the substrate and lubricating layers on the substrate form a slippery surface that resists adhesion by molecules and particles, and repels certain immiscible fluids. This allows the passage of materials at various flow rates, including high flow rates, without allowing the material to adhere to, attach, foul the surface, or, in the case of biological fluids such as blood, coagulate.

As used herein, reference to an "environmental material" or "environmental liquid" indicates a fluid or solid or other material, for which the ultra slippery layer according to the disclosure is designed to repel or reduce adhesion. Other terms, such as "repellent material," "repellent liquid," "material to be repelled," "fluid to be repelled," "liquid to be repelled," and the like, are meant to denote such similar materials.

In one embodiment, perfluorocarbon ("PFC") oil is used as the lubricating liquid, particularly when the materials to be repelled or excluded are immiscible in oleophobic liquids. The "Teflon-like" PFC oil is retained on the surface by a "Teflon-like" layer on the surface, e.g., a fluorous surface, which serves as the anchoring layer. The treated fluorous surface has an affinity for other fluorocarbons, and thus when PFC oil is applied to the treated surface, the surface is wetted by and retains a thin layer of PFC oil that resists adhesion of liquids and repels materials.

Substrate

Many types of substrates can be used in accordance with this disclosure. Generally, solids having chemically reactive surfaces (or surfaces that can be activated to provide chemically reactive surfaces) can be used to interact with and immobilize the anchoring layer and the lubricating layer applied to the surface. In one embodiment, the surface is smooth. In other embodiments, the surface is not limited to any degree of surface roughness.

The liquid repellant surfaces disclosed herein have properties that are independent of the geometry of the underlying substrate. Thus, the geometry of the substrate can be any shape, form, or configuration to suit the configuration of a variety of materials. Non-limiting examples of shapes, forms, and configurations that liquid repellant surfaces can take include generally spherical (e.g., beads, droplets, bubbles, drug or dye particles), tubular (e.g., for a cannula, connector, catheter, needle, capillary tube, hollow fiber, carbon nanotube or syringe), planar (e.g., for application to a microscope slide, plate, wafer, film, or laboratory work surface), or arbitrarily shaped (e.g., well, well plate, Petri dish, tile, jar, flask, beaker, vial, test tube, column, container, cuvette, bottle, drum, vat, or tank). The substrate can be a solid that is flexible or rigid.

In some embodiments, the substrate is flexible, such as for example, a flexible tube or tubing used in medical applications or a flexible diaphragm or valve used in a pump.

In some embodiments, the substrate is immiscible with the lubricating liquid such that the lubricating liquid does not wet or adhere to the substrate.

The substrate can be any material that is capable of surface modification to form the immobilized molecular anchoring layer. Many suitable materials are commercially available, or can be made by a variety of manufacturing techniques known in the art. Non-limiting examples of surfaces that can be used to prepare the ultra-slippery surfaces described herein include, e.g., glass, polymers (e.g., polysulfone, polystyrene, polydimethylsiloxane ("PDMS"), polycarbonate, polymethylmethacrylate, polyethylene, polypropylene, polyethylene terephthalate, polyvinyl chloride, styrene-ethylene/butylene-styrene, styrene-ethylene/ propylene-styrene, polyurethane, silicone, etc.), pure metals (e.g., titanium, gold, platinum, silver, aluminum, lithium, copper, beryllium, sodium, magnesium, calcium, potassium, gallium, etc.), metal alloys (e.g., stainless steel, nitinol, titanium, gold, platinum, silver, aluminum, cobalt-chrome, permalloy, aluminum alloys, beryllium alloys, magnesium alloys, lithium alloys, etc.), metalloids (e.g., boron, silicon, germanium, arsenic, antimony and tellurium, etc.), metalloid oxides (e.g., silica, quartz, borosilicate, silicon oxide, germanium oxide, boron oxide, etc.), paper, plastics, various forms of carbon (e.g, diamond, graphite, black carbon, fullerene, nanotubes, graphene, etc.), metal oxides (e.g., zinc oxide, copper oxide, ferric oxide, ferrous oxide, aluminum oxide, etc.) and other ceramic materials, composite materials (e.g., superparamagnetic materials, Janus particles, etc.), combinations of the above, and the like.

In certain environments, the substrate is selected to be compatible with the intended use of the device. For example, in medical devices, it is preferred that the solid material comply with FDA standards for safety and biocompatibility.

Suitable substrates contain reactive surface moieties in their native forms, or can be treated to provide suitable reactive moieties for linking with the anchoring compound. Exemplary reactive surface moieties include oxygen-containing surface groups such as oxides, hydroxides, carboxyl, carbonyl, phenol, epoxy, quinone and lactone groups and the like; nitrogen-containing surface groups such as amino, C=N groups, azides, amides, nitrile groups, pyrrole-like structure and the like, sulfur-containing moieties such as thiols, and the like, and reactive carbon containing surface groups such as alkynes and alkenes.

Surfaces can be treated to activate the surface and render it amenable to surface modification using well-understood techniques. Exemplary surface treatments include acid or base treatment, heat, ion bombardment, electron, electromagnetic, photon, oxidization, ammonization, plasma, microwave treatment, and various etching techniques.

Anchoring Molecules

According to one or more embodiments, the substrate is modified by providing an anchoring layer that has an affinity for and an ability to retain a lubricating liquid, on the substrate. Materials known to have strong omniphobic properties do not adhere to or spread out well on most hydrophilic or hydrophobic substrates. Similarly, materials known to have strong hydrophobic properties do not adhere to or spread out well on most hydrophilic or omniphobic substrates, and materials known to have strong hydrophilic properties do not adhere to or spread out well on most hydrophobic or omniphobic substrates. The selection of the appropriate immobilized molecular anchoring layer can improve the wetting properties of such liquids and thereby provide a surface with excellent liquid repelling properties.

Generally, the anchoring layer comprises anchoring molecules having a head group that binds (e.g., covalent bonds) to the substrate, and a functional tail group that non-covalently interacts with the lubricating layer to retain the lubricating layer on the surface. This anchoring layer forms at least a monomolecular layer on the substrate. In some embodiments, this layer forms more than a monomolecular layer on the substrate.

In some embodiments, the anchoring layer forms a covalent bond with the underlying substrate. The anchoring layer can be prepared by reaction of a reactive head group ("R2" in FIG. 2) of a bifunctional molecule bearing the functional tail, with a reactive species ("R1" in FIG. 2) on the surface of the substrate 210. The reaction of R2 and R1 forms a covalent linkage 220 that secures the functional group on the surface of the substrate. For example, reactive oxygen moieties on the surface ("R1") react with the trichlorosilane moieties ("R2") of a perfluorinated or polyfluorinated organosilane, to form a siloxy (Si—O) linkage and rendering a modified surface of exposed perfluorinated or polyfluorinated tails.

By way of example, the reactive head group (R2) is a group that reacts with oxygen-containing surface groups (R1) such as oxides, hydroxides, carboxyl, carbonyl, phenol, epoxy, quinone and lactone groups and the like; nitrogen-containing surface groups (R1) such as amino, C=N groups, amides, azides, nitrile groups, pyrrole-like structure and the like, sulfur-containing moieties such as thiols, and the like that are on the surface of the substrate, and reactive carbon containing surface groups such as alkynes and alkenes.

Some examples of groups that form upon reaction of R1 with R2 include ethers, silyl ethers, siloxanes, esters of carboxylic acids, esters of sulfonic acids, esters of sulfinic acids, esters of sulfuric acids, esters of phosphonic acids, esters of phosphinic acids, esters of phosphoric acids, silyl esters of carboxylic acids, silyl esters of sulfonic acids, silyl esters of sulfinic acids, silyl esters of sulfuric acids, silyl esters of phosphonic acids, silyl esters of phosphinic acids, silyl esters of phosphoric acids, oxides, sulfides, carbocycles, heterocycles with at least one oxygen atom, heterocycles with at least one nitrogen atom, heterocycles with at least one sulfur atom, heterocycles with at least one silicon atom, 'click' reactions-derived heterocycles, Diels-Alder reactions-derived carbocycles, Diels-Alder reactions-derived heterocycles, amides, imides, sulfides, thiolates, metal thiolates, urethanes, oximes, hydrazides, hydrazones, physisorbed or chemisorbed or otherwise non-covalently attached moieties, or combinations thereof.

Non-limiting examples for R2 include carboxylic acids, amines, halides, silanols, thiols, carbonyls, alcohols, phosphonic acids, sulfonic acids, inorganic oxides (e.g., silica, titania, alumina, zirconia, etc.), reactive metals (e.g., gold, platinum, silver), azides, alkenes, alkynes, and Zwitter ions, such as carboxy-betaines, glycine-betaines and sulfo-betaines.

For example, the surfaces with hydroxyl groups (i.e., —OH) can be functionalized with various commercially available substances such as polyfluoroalkylsilanes (e.g., tridecafluoro-1,1,2,2-tetrahydrooctyl-trichlorosilane, heptadecafluoro-1,1,2,2-tetra-hydrodecyl trichlorosilane, etc.), alkylsilanes, aminosilanes (e.g., (3-aminopropyl)-triethoxysilane, 3-(2-aminoethyl)-aminopropyltrimethoxysilane), glycidoxysilanes (e.g., (3-glycidoxypropyl)-dimethylethoxysilane), and (mercaptoalkyl)silanes (e.g., (3-mercaptopropyl)-trimethoxysilane). In certain embodiments, a variety of materials that have or can easily form oxides on the surface, such as silicon, glass, alumina, and organic polymers, can be activated to contain —OH functional groups using techniques such a plasma treatment. After activation, either vapor or solution deposition techniques can be used to attach various organosilyl moieties to the substrates. Organosilyl moieties can be chosen from perfluorinated, partially fluorinated or non fluorinated ones.

In certain embodiments, non-limiting examples for R2 include thiol groups that reacts with metal substrates, such as gold, copper, silver, platinum, palladium, rhodium, ruthenium, their alloys and intermetallic compounds.

In another embodiment, non-limiting list of exemplary reactive group (R2) includes substituted or unsubstituted carboxylic acids, substituted or unsubstituted sulfonic acids, substituted sulfinic acids, substituted sulfuric acids, substituted phosphonic acids, substituted phosphinic acids, substituted phosphoric acids, and their respective esters, or combinations thereof.

In one or more embodiments, the anchoring layer includes a perfluorocarbon or fluorocarbon tail having a tail length of at least one carbon. In specific embodiments, the perfluorocarbon tail can have a carbon length of 1-50, or 2-20 or 4-16 or 6-12. In one or more embodiments, the anchoring group head group is a siloxy group (Si—O) formed in the reaction of a reactive silane group, e.g., trichlorosilane, with oxygen moieties on the substrate surface. A number of commercially available perfluorocarbon trichlorosilanes are available. As used herein, reference to a "silanized" surface indicates an anchoring layer in which the head group includes and Si—O linkage.

In other embodiments, crosslinking agents can be used to link the reactive surface with the anchoring layer molecules. For example, as shown below, bifunctional linkers such as epichlorohydrin, glutaraldehyde, adipic dihydrazide can attach hydroxyl-, amino- and carboxylic acid terminated compounds to their respectively activated surfaces.

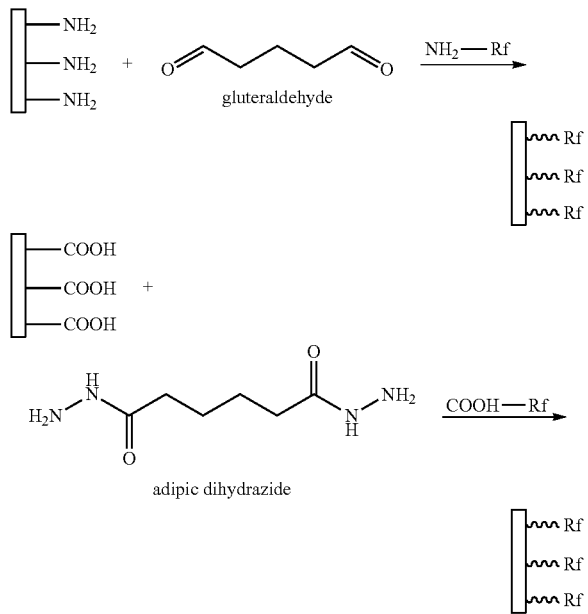

Table 1 shows additional examples of linking chemicals. A non-limiting list of exemplary linking reagents with the same or different reactive groups at either end are shown. The reagents are classified by which chemical groups link (left column) and their chemical composition (right column).

TABLE 1

| Crosslinking Target | Linker Reactive Groups, Features |
|---|---|
| Amine-to-Amine | NHS esters |
|  | Imidoesters |
| Sulfhydryl-to-Sulfhydryl | Maleimides |
| Nonselective | Aryl azides |
| Amine-to-Sulfhydryl | NHS ester/Maleimide |
|  | NHS ester/Pyridyldithiol |
|  | NHS esters/Haloacetyl |
| Amine-to-Nonselective | NHS ester/Aryl Azide |
|  | NHS ester/Diazirine |
| Amine-to-Carboxyl | Carbodiimide |

TABLE 1-continued

| Crosslinking Target | Linker Reactive Groups, Features |
|---|---|
| Sulfhydryl-to-Carbohydrate | Maleimide/Hydrazide |
|  | Pyridyldithiol/Hydrazide |
| Amine-to-DNA | NHS ester/Psoralen |

The functional tail group of the anchoring molecules can be selected to have an affinity, such as non-covalent interaction, with molecules of the lubricating layer and retain the lubricating layer on the surface. As used herein, high affinity refers to the spreading coefficient of the lubricant over that of the functional group is positive, such as having attractive forces and generally miscible with one another, such that the lubricating liquid has a greater adsorption equilibrium constant with the functional group of the anchoring layer than the material to be repelled does to the functional group of the anchoring layer. Particularly, a no-slip condition can develop between the lubricating liquid and the anchoring layer so that there is an outermost molecules of the lubricating liquid that is stuck to the anchoring layer although other parts of the lubricating liquid may be forced away from the substrate (e.g., shear deformation, high impact pressure, etc.) For example, functional groups comprising hydrocarbons such as alkanes, alkenes, alkynes, and aromatic compounds, and combinations thereof can be used to create a hydrophobic surface that has an affinity for lubricating liquids that are also hydrophobic or lypophilic. The combined surface layer and lubricating liquid is useful for repelling hydrophilic or omniphobic fluids. In another embodiment, hydrophilic functional groups can be used to create a hydrophilic surface that has an affinity for hydrophilic liquids. Exemplary hydrophilic groups include charged polypeptides, polyanions (e.g., heparin sulfate, oligonucleotides, dextran sulfate), polycations (e.g. chitosan, chitin, hexadimethrine bromide, diethylaminoethyl cellulose) polar polymers (polyacrylamide, polyethylene glycol, polypropylene glycol), polysaccharides (dextran, agarose, inulin, sepharose), amines (e.g. aminopropyl, diethylaminoethanol), carboxylic acids, guanidine, alcohols, sulfhydryls, carboxamides, and metal oxides. The combined surface layer and lubricating liquid is useful for repelling hydrophobic or omniphobic fluids. In still another embodiment, functional groups comprise perfluorinated groups (e.g., perfluoropoly (or oligo) ethers, etc.) that have affinity to lubricants to create an omniphobic surface for repelling hydrophilic or hydrophobic fluids.

The substrate can be coated with the anchoring layer by methods well known in the art, including plasma-assisted chemical vapor deposition, chemical functionalization, chemical solution deposition, chemical vapor deposition, chemical cross linking, and atomic layer deposition. For example, chemical vapor deposition can be carried out by exposing the substrate to reactive silane vapors. For chemical solution deposition, the deposition can be carried out by, e.g., immersing the substrate in a silane solution followed by rinsing and drying. Similarly, other reactive head groups can be brought in contact and made to react with the surface by using gas- and solution-phase methods well-established in the art.

The anchoring layer can be applied in a thickness sufficient to cover the surface of the substrate. The actual thickness of the applied layer may be a function of the method of application. The anchoring layer applied in a typical thickness is assumed to be a monomolecular layer, however, the layer may not completely cover the entire surface but still be sufficient to modify the surface properties of the substrate. Similarly, the layer may be more than one monomolecular layer.

Certain embodiments may involve reacting perfluoroalkylamines, with carbon chain lengths ranging from ethyl to dodecyl, such as 1H,1H-perfluorooctylamine, to different surfaces like polyesters, polyurethanes, or polyvinylchloride through aminolysis of the esters and carbamates in the backbone or nucleophilic substitution.

In certain embodiments, the underlying substrate functionalized with the desired anchoring layer via a two-step process, such as by reacting the substrate surface to provide a desired reactive moiety, which can then be further reacted with the desired anchoring layer. For example, an underlying substrate (e.g., silica) can be reacted to provide an isocyanate group, which can then be utilized to carry out a carbamation reaction between hydroxyl or amino terminated fluoro compound (HO—Rf and $NH_2$—Rf) and isocyanatopropyl triethoxysilane (ICPTES) to form fluorosilane linker through urethane and urea formation respectively.

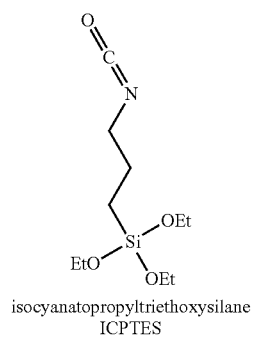

isocyanatopropyltriethoxysilane
ICPTES

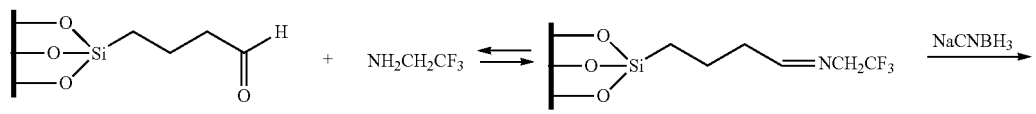

Rf: Fluoro group such as: $H(CF_2CF_2)$ in $CH_2$, in which n = 1-8, or PFE derivatives As another example, as shown below, hydroxylated surfaces can be functionalized with triethoxysilyl butyraldehyde (ABTES) and further reacted with amino terminated fluoro compounds.

In certain embodiments, perfluoroalkylamines can react with surfaces bearing acrylates, maleimides, carboxylic acids, anhydrides, aldehydes, and epoxides through Michael addition, amidation, nucleophilic addition, and ring-opening mechanisms.

Other nucleophilic perfluorinated molecules include perfluoroalkylthiols such as perfluorodecanethiol that may react with electrophiles such as maleimides as well as disulfide-containing substrates.

In certain embodiments, perfluoroalkyl alcohols like 1H,1H,2H,2H-perfluoro-1-octanol could be anchored to carboxylic acid-containing substrates through esterification.

In certain embodiments, substrates containing amines and relevant nucleophiles can react with perfluoroalkylacrylates, ranging in carbon chain length from ethyl to dodecyl, such as 1,1,1,3,3,3-hexafluoroisopropyl acrylate, or perfluoroalkylepoxides, such as perfluorohexyl propyl epoxide or perfluorooctyl propyl epoxide.

In certain embodiments, perfluoroalkyliodides, with chain lengths ranging from ethyl to dodecyl, such as 2-(perfluorooctyl)ethyl iodide, may be reacted with olefin-bearing surfaces to yield iodide adducts in the presence of an amine and metal salt.

Hydrocarbon analogs of the aforementioned reactions may readily be obtained as well using fatty acids, lipids, alkylamines, alkanethiols, alkyl alcohols, alkyl halides, alkyl acrylates, and alkyl epoxides with varying carbon chain lengths, ranging from C2 to C22.

In certain embodiments, phosphonic acids can be utilized as part of the anchoring layer. As used herein, the term "phosphonic acid" refers to an organic compound having the structure:

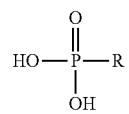

wherein R is an organic (carbon-containing) radical or residue wherein the phosphorus atom is bonded to a carbon atom of the R group. Those of ordinary skill in the art are aware that the hydrogens attached to the OH groups of phosphonic acids are acidic and can be removed by bases or at appropriate pH's to form salts of the phosphonic acids having phosphonate mono or di-anions having the structure:

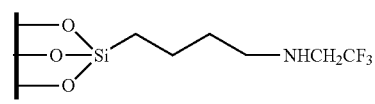

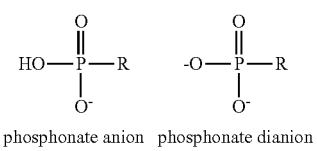

phosphonate anion    phosphonate dianion

It is understood that, when present as an anion, the phosphate can include one or more associated counter ions, for example, monovalent cations including lithium, sodium, or potassium or one or more divalent cations including calcium or zinc. The organic "R" radical or residue comprises at least one carbon atom, and includes but is not limited to the many well-known carbon-containing groups, residues, or radicals well known to those of ordinary skill in the art. The R radicals can contain various heteroatoms, or be bonded to another molecule through a heteroatom, including oxygen, nitrogen, sulfur, phosphorus, or the like. Examples of suitable R radicals include but are not limited to alkyls such as methyl, butyl, or octadecyl radicals and the like, or substituted alkyls such as hydroxymethyls, haloalkyls, perfluoroalkyls, aromatics such as phenyls or substituted aromatics, such as phenols or anilines; or polymeric residues such as PEG, PPG, silicone, polyethylene, fluoropolymers such as perfluoropolyethers, Teflons or Vitons, polycarbonates, etc, and the like. In many non-polymeric embodiments, the R radicals of the phosphonates comprise 1 to 18 carbon atoms, 1 to 15, carbon atoms, 1 to 12 carbon atoms, 1 to 8 carbon atoms, or 1 to 4 carbon atoms.

In certain embodiments, phosphonic acid ligands can be attached to metal oxide substrate surfaces.

In another aspect, the phosphonic acid ligands can form a coating on the surface of metal oxide substrates.

In a further aspect, at least one phosphonic acid ligand comprises a residue of a compound having the structure $R_n$—$X_n$, wherein R is a ligand group and X is a phosphonic acid group having the structure:

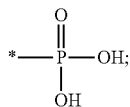

and
wherein each n is, independently, 1, 2, or 3.

In a yet further aspect, each n is 1. In a still further aspect, the compound comprises the structure R—X.

In one aspect, a chemically functionalized substrate of the invention can comprise at least one phosphonic acid ligand.

In a further aspect, a chemically functionalized substrate of the invention can comprise a plurality of phosphonic acid ligands.

In yet another aspect, a chemically functionalized substrate of the invention can be covered with phosphonic acid ligands.

In yet a further aspect, a chemically functionalized substrate of the invention can be covered with a mixture of more than one type of phosphonic acid ligands.

The term "phosphonic acid ligand" as used herein refers to a radical or residue attached to or capable of attaching to the surface of the metal oxide substrates that is derived from a phosphonic acid. Those of ordinary skill in the art will understand that phosphonic acids or their anionic salts can be readily attached to a surface of a metal oxide, by replacement of one or more of the oxygen atoms of the phosphonic acid with bonds ranging from covalent, to polar covalent, to ionic, and including through hydrogen bonding, between the phosphorus atom and an oxygen atom or ion on a metal oxide surface.

In certain aspects, at least one organic phosphonic acid comprises methylphosphonic acid, octylphosphonic acid, decylphosphonic acid, octadecylphosphonic acid, phenylphosphonic acid, benzylphosphonic acid, pentafluorobenzylphosphonic acid, 11-hydroxyundecylphosphonic acid, (11-phosphonoundecyl)phosphonic acid, (3,3,4,4,5,5,6,6,7,7,8,8,8-tridecafluorooctyl)phosphonic acid, pentabromobenzylphosphonic acid, (11-acryloyloxyundecyl)phosphonic acid, or a mixture thereof.

In one aspect, the phosphonic acid ligands are attached to the surface by bonding of one, two, or three of the oxygen atoms of the phosphonic acid ligands to the metal oxide surface. For example, the organic phosphonic acid ligands can be attached to the surface by bonds ranging from covalent, to polar covalent, to ionic, and including through hydrogen bonding, as illustrated by one or more of the structures illustrated below:

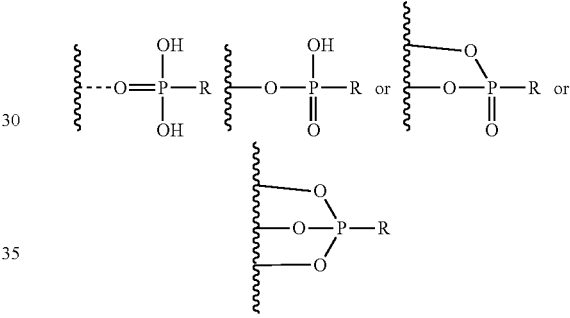

In one aspect, R can be an organic radical comprising 1 to 18 carbon atoms, for example, an organic radical comprising 1 to 16 carbons, 1 to 14 carbons, 1 to 12 carbons, 1 to 10 carbons, 1 to 8 carbons, 1 to 6 carbons, or 1 to 4 carbons.

In a further aspect, R is an alkyl substituted polyether having the structure:

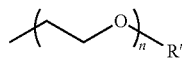

wherein n is 1 to 25 (including 1, 2, 3, 4, 5, 6, 7, 8, 9, 10, 11, 12, 13, 14, 15, 16, 17, 18, 19, 20, 21, 22, 23, 24, and 25), and R' is a C1-C4 alkyl (including 1, 2, 3, or 4 carbons). In a yet further aspect, R is selected from methyl, ethyl propyl, butyl, pentyl, hexyl, heptyl, octyl, nonyl, decyl, undecyl, and dodecyl.

In another aspect, R comprises a substituted or unsubstituted, linear or branched, $C_3$ to $C_{50}$ aliphatic or cyclic aliphatic, fluoroalkyl, oligo(ethyleneglycol), aryl, or amino group.

In another aspect, R can comprise linear or branched alkyl groups having up to 12 carbons (including 1, 2, 3, 4, 5, 6, 7, 8, 9, 10, 11, and 12 carbons) or having up to 8 carbons (including 1, 2, 3, 4, 5, 6, 7, and 8 carbons), and α and β can be, independently, integers from 1 to 12 (including 1, 2, 3, 4, 5, 6, 7, 8, 9, 10, 11, and 12) or integers from 1 to 8 (including 1, 2, 3, 4, 5, 6, 7, and 8).

In a further aspect, R is a fluorinated group. For example, R can comprise —$(CH_2)_\beta$—$(OCH_2CH_2)_\alpha F$, —$OCHCH_2$—$(CF_2)_\beta CF_3$, —$(CF_2CF_2)_\beta$, —$(CF_2)_\beta CF_3$, —$(CF_2)_\beta$—$(CF_2CF_2)_\alpha CF_3$, —$(CF_2CF_2)_\alpha$, —$(CH_2)_\beta CF_3$, or —$(CF_2)_\beta$—$(CF_2CF_2)_\alpha CF_3$, wherein α is an integer from 0 to 25 and wherein β is an integer from 0 to 25. In various further aspects, α and β can be, independently, integers from 1 to 12 (including 1, 2, 3, 4, 5, 6, 7, 8, 9, 10, 11, and 12) or integers from 1 to 8 (including 1, 2, 3, 4, 5, 6, 7, and 8).

Crosslinking Agents

Figure 2:
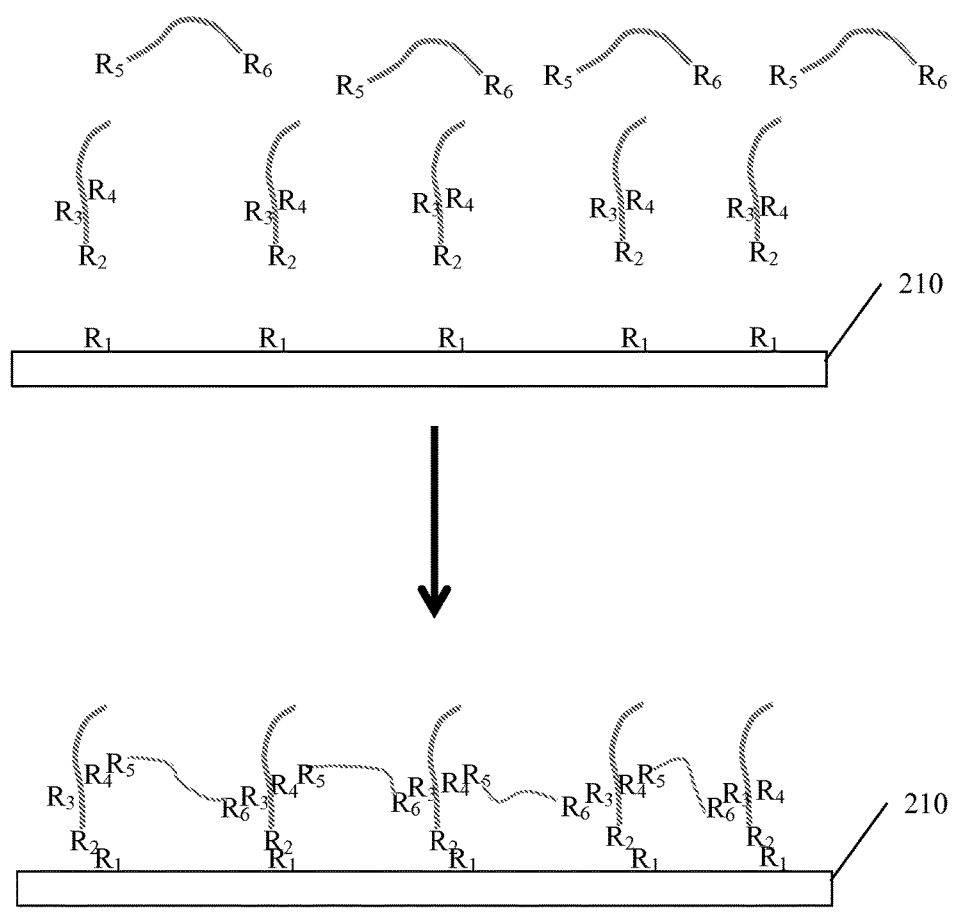
FIG. 2 is a schematic illustration of the reaction that occurs to obtain an anchoring layer of crosslinked immobilized molecules in accordance with certain embodiments.

According to one or more embodiments, the anchoring layer further comprises one or more crosslinking agents that can crosslink the anchoring molecules to each other. As shown in FIG. 2, the anchoring molecules have further reactive groups ("R3" and "R4" in FIG. 2) that can react with one or more crosslinking agents to form a crosslinked network. The crosslinking agent includes at least two functional groups ("R5" and "R6" in FIG. 2) that react with the reactive groups found on the anchoring molecules. For example, molecules having diol functional groups can be utilized as crosslinking agents when the anchoring molecules have at least two chlorinated groups that can react with the diol groups to form a crosslinked network.

In certain embodiments, the crosslinking agents may be short chained molecules having at least a bifunctional group. In certain embodiments, the crosslinking agents may be medium chained molecules having at least a bifunctional group. In certain embodiments, the crosslinking agent may be long chained polymeric molecules having at least a bifunctional group. In certain instances, the crosslinking agent may have higher molecular weight than that of the individual anchoring molecules.

In certain embodiments, the crosslinking agent can have molecular components that provide affinity with the lubricating liquid. For example, if the crosslinking agent is an oligomer or a polymer, the molecular components may be additional repeat units between the functional groups of the crosslinking agents that provide further affinity with the lubricating liquid.

In alternative embodiments, the crosslinking agent can have molecular components that do not provide affinity with the lubricating liquid. For example, if the crosslinking agent is an oligomer or a polymer, the molecular components may be contain repeat units between the functional groups of the crosslinking agents that do not provide further affinity with the lubricating liquid. In some cases, the crosslinking agents can be immiscible with the lubricating liquid.

In further alternative embodiments, the crosslinking agent can have molecular components that have an affinity with the repellent material. For example, if the crosslinking agent is an oligomer or a polymer, the molecular components may be contain repeat units between the functional groups of the crosslinking agents that have an affinity with one or more components contained in the repellent material. In some cases, the crosslinking agents can be miscible with the repellent material.

Some other suitable crosslinking agents, along with the corresponding functional groups of the anchoring molecules, are shown in Table 2 below.

TABLE 2

| Crosslinking Agent Functional Groups | Reactive Groups in the Anchoring Molecules |
| --- | --- |
| Alcohol | Acyl halide, silanol, silyl halide, |
| Amine | Acyl halide, silanol, silyl halide, |

TABLE 2-continued

| Crosslinking Agent Functional Groups | Reactive Groups in the Anchoring Molecules |
| --- | --- |
| Carboxylic acid | Acyl halide, silanol, silyl halide, |
| Silanol | Alcohol, amine, carboxylic acid |
| Phosphate | Alcohol, amine, carboxylic acid |
| Sulfonate | Alcohol, amine, carboxylic acid |
| Aminooxy | Azide |
| Thiol | Thiol, gold, NHS-ester |
| Isocyanate | Alcohol, amine, silanol, carboxylic acid |
| Alcohol, amine, silanol, carboxylic acid | Isocyanate |

In certain embodiments, the crosslinking agent can be polyethylene glycol diol, ethylene glycol, polypropylene gylcol, perfluoroglutamic acid, perfluoropolyether (Krytox), hydroxyl terminated polydimethylsiloxane, amine terminated polydimethylsiloxane, polysulfone, polyethersulfone, polymethylmethacrylate, polyacrylimide, polybutadiene, water, formamide, gluteraldehyde, acetic acid, biopolymer, proteoglycan, cellulose, keratin, chitosan, chitin, polylactic acid, protein, immunoglobulin, heparin, heparin sulfate, poly(N-isopropylacrylamide), polyurethane, metals and metal oxides (e.g. ferric oxide, ferrous oxide, cupric oxide, aluminum, aluminum oxide, zinc oxide, zinc, magnesium, calcium, and the like), alginate, silk, glycosaminoglycans, keratin, silicates, and the like.

In certain embodiments, the crosslinking agent can be a fluorocarbon polymer or a polymer containing fluorous groups. For example, the crosslinking agent may be fluoroalkanes, fluoroalkynes, fluoralkenes, perfluoropolyether, or combinations thereof.

In certain embodiments, the crosslinking agent can be a hydrophobic polymers or a polymer containing hydrophobic groups. For example, the crosslinking agent may be branched or linear alkanes, alkynes, alkenes, aromatics or combinations thereof. In certain embodiments, the crosslinking agent can be a thermosetting polymers, such as polyurethanes, rubber, epoxy, polyimides, polyesters or combinations thereof. In certain embodiments, the crosslinking agent can be a thermoplastic polymer, such as acrylic, nylon, polypropylene, polystyrene, polyvinyl chloride, polybenzimidazole, polycarbonate, polysulfone, polyethersulfone, polyether ether ketone, polyetherimide, poly dimethylsiloxane (PDMS), poly(tetramethylene ether) glycol, or combinations thereof.

In certain embodiments, the crosslinking agent can be a hydrophilic polymer or a polymer containing hydrophilic groups. For example, the crosslinking agent can be a polyethylene glycol, monoethylene glycol, saccharides, polysaccharides and modified polysaccharides, (e.g. dextran, cellulose, methylcellulose, agarose, chitosan, chitin, heparin, heparan sulfate, glycosaminoglycans, mucopolysaccharides, alginate, chondroitin sulfate, dermatan sulfate, keratan sulfate, Hyaluronan, alginate, galactuonic acid), polyacrylamide, polyvinyl alcohol, poly(lactic-co-glycolic acid), polylactide, poly-glycolide, polybrene, Polyethylenimine, poly(amidoamine), poly(N-isopropylacrylamide), N,N'-methylene-bis-acrylamide, N,N'-cystamine-bis-acrylamide, 1,4-butanediol, polar methacrylates (polysulfobutaine methacrylate, polycarboxybetaine methacrylate, poly(methoxyethyl acrylate),), phosphocholine-containing polymers, poly(ester urethane) urea, polycapprolactone, polypeptides, oligonucleotides, laminin, collagen, fibrinogen, fibronectin, polybetaine and betaine containing polymers, betaines, or combinations thereof.

In certain embodiments, the crosslinking agent can have two reactive moieties to bond to the anchoring layer. In other embodiments, the crosslinking agent can have 3 or more bonds to the anchoring layer.

Lubricating Layer

The lubricating liquid used to form the lubricating layer is applied to the anchoring layer. Thus, the lubricating layer, which flows readily over the substrate, can stably, but non-covalently bind to the functional group of the anchoring layer to form a continuous, repellant layer. The lubricating layer can be selected based on its ability to repel immiscible materials. In one or more embodiments, the lubricating layer is inert with respect to the underlying substrate and environmental material to be repelled.

The lubricating layer can be prepared from a variety of fluids. In one or more embodiments, the ultra-slippery surface is used in a medical setting, in which case the lubricating liquid is selected, e.g., based on its biocompatibility, level of toxicity, anti-coagulation properties, and chemical stability under physiologic conditions. For example, compounds that are approved for use in biomedical applications can be used in accordance with the present disclosure. Perfluorinated organic liquids, in particular, are suitable for use in biomedical applications. In some aspects, the lubricating layer is perfluorinated oil, non-limiting examples of which include PFC oils such as FC-43, FC-70, perfluorotripropylamine, perfluorotripentylamine, perfluorotributylamine, perfluorodecalin, perfluorooctane, perfluorobutane, perfluoropropane, perfluoropentane, perfluorohexane, perfluoroheptane, perfluorononane, perfluorodecane, perfluorododecane, perfluorooctyl bromide, perfluoro(2-butyl-tetrahydrofurane), perfluoroperhydrophenanthrene, perfluoroethylcyclohexane, perfluoro(butyltetrahydrofuran), perfluoropolyethers (KRYTOX), and combinations thereof. In other aspects, the lubricating layer is fluorinated organic liquid, non-limiting examples of which include fluorinated hydrocarbon oils such as 3-ethoxy-1,1,1,2,3,4,4,5,5,6,6,6-dodecafluoro-2-trifluoromethyl-hexane, trifluoromethane, difluoromethane, pentafluoroethane, hydrofluoroether, etc. In other aspects, the lubricating layer is hydrocarbon oil, non-limiting examples of which include oils such as alkanes (e.g., butane, pentane, hexane, cyclohexane, heptane, octane, nonane, decane, dodecane, hexadecane, octadecane), triacylglycerides, mineral oil, alkenes, cholesterol, aromatic hydrocarbons (e.g., benzene, phenol, naphthalene, naphthol,) and combinations thereof. In other aspects, the lubricating layer is a hydrophilic liquid, non-limiting examples of which include water, aqueous solutions (e.g., acids, bases, salts, polymers, buffers), ethanol, methanol, glycerol, ionic liquids (e.g., ethylammonium nitrate, ethylmethylimidazolium hexafluorophosphate, 1-butyl-3-methylimidazolium hexafluorophosphate; for other examples of ionic liquids that can be used see: "Ionic Liquids in Synthesis" P. Wasserscheid and T. Welton (Editors), Wiley-VCH; 2 edition (Nov. 28, 2007), the contents of which is incorporated by reference herein), and combinations thereof.

In some aspects, the viscosity of the lubricating layer can be chosen for particular applications. For example, the viscosity of the lubricating oil can be <1 cSt, <10 cSt, <100 cSt, <1000 cSt, or <10,000 cSt.

In some aspects, the lubricating layer has a low freezing temperature, such as less than −5° C., −25° C., or −50° C. A lubricating layer with a low freezing temperature allows the layer to remain liquid in low temperatures to maintain the ability of the combination of the lubricating layer and functionalized surface to repel a variety of liquids or solidified fluids, such as ice and the like.

In some aspects, the lubricating layer has a low evaporation rate or a low vapor pressure. For example, the vapor pressure of the lubricating liquid can be less than 10 mmHg at 25° C., less than 5 mmHg at 25° C., less than 2 mmHg at 25° C., less than 1 mmHg at 25° C., less than 0.5 mmHg at 25° C., or less than 0.1 mmHg at 25° C. The lubricating layer can be applied in a thickness sufficient to cover the anchoring layer. In some embodiments, the lubricating layer is applied at a thickness sufficient to form a monomolecular layer on the substrate. In other embodiments, the lubricating layer is applied at a thickness of 10 nm to 10 μm on the substrate. In other embodiments, the lubricating layer is applied at a thickness of 10 μm to 10 mm on the substrate. The lubricating layer applied in a typical thickness, assumed to be a monomolecular layer, can remain liquid repellant for a long period without requiring replenishing. By way of example, the surface can remain liquid repellant for a period longer than 1 hour, or longer than 6 hours, or longer than 24 hours, longer than a week, or longer than a year or more.

The lubricating liquid can be sprayed, cast, or drawn onto the substrate either once or repeatedly. In certain embodiments, the lubricating layer can be applied to the surface by spinning coating, pipetting drops of lubricating liquid onto the surface, or dipping the surface into a reservoir or channel containing the lubricating liquid, through microscale holes in the wall of the underlying substrate, or by presaturating the surface with lubricating liquid to form a lubricating layer. The lubricating liquid can also be applied by absorption, wicking, thin layer deposition, or by intermittent passing of volumes of lubricating liquid over the surface (e.g., small plugs or bubbles flowing in a catheter). In some embodiments, any excess lubricating liquid can be removed by spinning the coated article or by drawing a squeegee across the surface or flushing and rising with another liquid.

In some embodiments, the lifetime of the liquid repellant surface can be extended by reapplying the lubricating layer at a certain interval. For example, a pump can be utilized so that lubricating liquid is periodically applied over the anchoring molecules. In some aspects, the lubricating layer is replenished every 1, 5, 10, 15, 20, 30, 40, 50, or 60 seconds. In other aspects, the lubricating layer is replenished every 5, 10, 15, 20, 30, 40, 50, or 60 minutes. In still other aspects, the lubricating layer is replenished every 2, 4, 6, 8, 10, 12, 24, 48, 60, or 72 hours or more. Yet in other aspects, the lubricating liquid can be replenished continuously, at a constant or varying rate. In other embodiments, the surface can be replenished with lubricating liquid from a reservoir 160 housed below the substrate 100 as shown in FIG. 1. The lubricating liquid is drawn through micropassages 150 to replenish lubricating liquid lost to the environment.

Additives

In certain embodiments, the lubricating layer, the anchoring layer, and/or the underlying substrate can contain one or more additives that can further promote the repellency of the repellent material.

In certain embodiments, the lubricating layer, the anchoring layer, and/or the underlying substrate can contain one or more additives that can be eluted over time into the repellent material. In certain instances, the additives can be certain molecules, drugs, pharmaceutical compositions that can be slowly eluted into the repellent material, such as blood.

Advantages

Without wishing to be bound by theory, the use of crosslinked anchoring molecules provides unexpectedly superior results over anchoring molecules that are not crosslinked with each other. First, the presence of crosslinks improves the mechanical stability of the anchoring molecules such that the anchoring layer that is able to attract the lubricating liquid is less prone to mechanical damage during use, such as through abrasion, impact, scratching, stretching and the like. In particular embodiments, use of a crosslinking agent that has desired mechanical robustness on its own (e.g., polymeric or oligomeric crosslinking agents, such as those discussed in various parts of this application), can provide further mechanical robustness when swelled with the lubricating liquid. Second, the presence of crosslinks improve the stability of the lubricating layer such that the lubricating layer is able to better maintain the liquid overlayer that provides the ultra-repellency. Use of the crosslinked anchoring molecules provides improved resistance to erosion of the lubricating liquid (e.g., shear erosion through flow of repellent liquid, such as blood, over the slippery surface) that can occur during normal use as compared to surfaces prepared using anchoring molecules that are not crosslinked with one another. Third, the presence of crosslinks provides further resistance against the evaporation of the lubricating liquid solvent as compared to surfaces prepared using anchoring molecules that are not crosslinked with one another. Fourth, the presence of crosslinks provides further resistance to dissolution of the lubricant into the repelled liquid and to formation and loss of lubricant droplets into the repelled liquid.

Moreover, the use of crosslinked anchoring layers that are bound to an underlying substrate provides improvements over other approaches. For example, use of a crosslinked polymer as the substrate itself can lead to degradation in various properties, such as mechanical stability, sizing requirements and the like. However, by providing only a thin anchoring layer that attracts the lubricating liquid over a substrate that is immiscible with the repelled liquid allows use of the apparatus in various constrained environments, such as in catheters, needles, and the like.

In certain embodiments, the use of the crosslinked anchoring layer can control the rate of elution of additives into the repellent material. By altering the degree of crosslink density, greater or lesser amount of additive entrainment, but eventual elution, into the repellent material can be provided. Hence, rate controlled release of drugs or pharmaceutical formulations into the repellent material, such as blood, can be controlled even more precisely over conventional systems.

In particular embodiments where crosslinking agents that are not miscible with the lubricating liquid are used, it is surprising that despite the use of crosslinking agents that are immiscible with the lubricating liquid, a crosslinked anchoring layer can nevertheless stably retain the lubricating liquid. However, by utilizing such material combinations, it has surprisingly been found that the system can provide further resistance to swelling of the anchoring layer to further maintain the size tolerances even with the presence of the anchoring layer thereon.

Uses

In one or more embodiments, any arbitrary liquid (e.g., a biological fluid), and solid particulates contained therein, may be strongly repelled from the surfaces modified in accordance with the present disclosure. Similarly, adhesion of one solid surface to another solid surface can be prevented, or the friction between two solid surfaces can be reduced using the methods disclosed herein.

Figure 3:
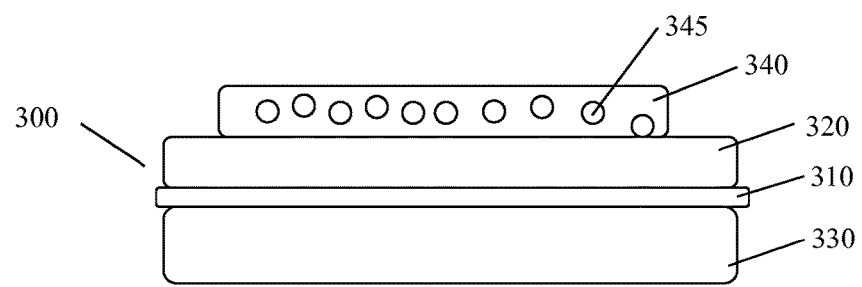
FIG. 3 is a schematic representation of an ultra-slippery surface that prevents repellent liquid, and solutes, solid particulates, or combinations thereof contained in the repellent liquid from adhering to a substrate in accordance with certain embodiments.

For example, FIG. 3 is a representation of an ultra-slippery surface 300 including an anchoring layer 310 and a lubricating layer 320 on a substrate 330 that is used to prevent an environmental liquid 340, and solutes and solid particulates 345 contained in liquid 340, from adhering to underlying substrate 330. Thus, solutions and suspensions can be prevented from adhering to the surface of articles that have been coated with the ultra-slippery coating according to one or more embodiments. In other embodiments, the ultra-slippery surface 300 provides a low friction interface with environmental liquid 340 (and the entrained solutes and particles 345).

Medical disciplines ranging from cardiovascular medicine and oncology to orthopedics and ophthalmology rely increasingly on the implantation of medical devices into coronary arteries, jugular and femoral veins, joints, and many other parts of the body. Use of these devices risks the development of implant-induced thrombogenesis, or blood clotting. Similarly, blood processing equipment such as blood dialysis instruments, in particular, dialysis catheters, must take precautions to prevent blood clotting. In particular, blood naturally coagulates when exposed to glass. In one application, surfaces that normally contact blood can be coated with the ultra slippery coating described herein to reduce thrombogenesis, e.g., blood clotting and coagulation. As demonstrated in the examples below, ultra slippery coatings using a crosslinked perfluorinated anchor layer and a perfluorohydrocarbon lubricating layer is highly effective in reducing thrombosis on surfaces that are in prolonged contact with unheparinized blood, even in flowing conditions.

Thus, the disclosed liquid repellant surfaces can be used in a number of biological applications, including preventing blood clotting, cell adhesion, bacterial adhesion, biofilm formation and fouling of most surfaces. Moreover, these surfaces do not require anticoagulants when used to prevent blood clot formation.

Figure 4:
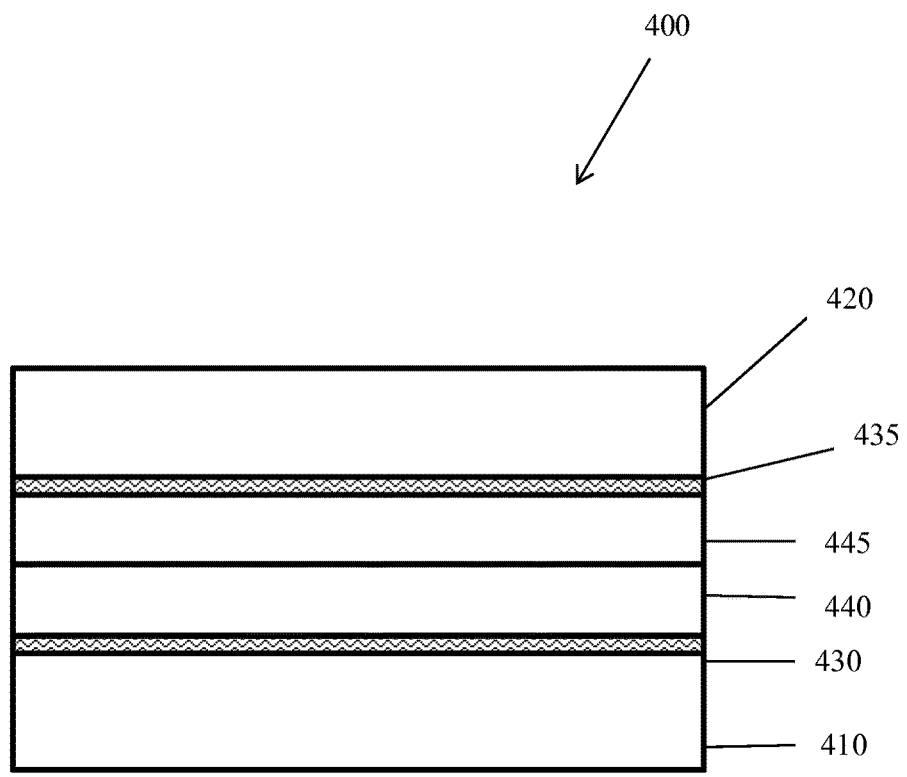
FIG. 4 is a schematic illustration of ultra-slippery surfaces that prevent two substrates from adhering to one another in accordance with certain embodiments.

In another embodiment, the surfaces described in accordance with the present disclosure can be used to prevent two substrates from adhering, or to reduce the friction between two substrates. FIG. 4 is a schematic illustration of an ultra-slippery surface 400 used to prevent a first substrate 410 and a second substrate 420 from sticking. Each of solid substrates, 410, 420, possess an ultra slippery surface including anchoring layers 430, 435, respectively, that are crosslinked and that interacts with and retains lubricating liquids, 440, 445, respectively. Liquids 440, 445 are selected to be immiscible with one another. In addition, substrate 410 has a preferential affinity for lubricating liquid 440, while substrate 420 has a preferential affinity for lubricating liquid 445. When substrates 410, 420 are in facing relationship with one another, the liquid/liquid interface defined at lubricating liquids, 440, 445 allows the friction between the substrates to be reduced.

In some aspects, the surfaces are modified for potential applications such as low friction transport or repulsion of viscous liquids, non-viscous liquids, complex fluids, semi-solids, tacky liquids (e.g., food products, fuel products, resins, and the like), water (e.g., dew, fog, frost, ice and the like), paints, iron filings, carbon filings, dirt, debris, insects, for coating oil pipelines and tubing to prevent biofouling, in yacht and marine finishes, and the like. In certain embodiments, the ultra slippery coating can be formed on the interior surfaces of a food container. For example, commercially available plastic bottle made of polyethylene terephthalate ("PETE") can silanized and crosslinked to form a crosslinked fluorous surface and then treated with PFC oil to prevent adhesion of food items (e.g., ketchup) to the inner surface of the treated bottle.

In one or more of the above embodiments, non-limiting examples of surfaces that can be made liquid repellant include beads, cannula, connector, catheter (e.g., central line, peripherally inserted central catheter (PICC) line, urinary, vascular, peritoneal dialysis, and central venous catheters), catheter connector (e.g., Luer-Lok and needleless connectors), clamp, skin hook, cuff, retractor, shunt, needle, capillary tube, endotracheal tube, ventilator, associated ventilator tubing, drug delivery vehicle, syringe, microscope slide, plate, film, laboratory work surface, well, well plate, Petri dish, tile, jar, flask, beaker, vial, test tube, tubing connector, column, container, cuvette, bottle, drum, vat, tank, organ, organ implant, or organ component (e.g., intrauterine device, defibrillator, corneal, breast, knee replacement, and hip replacement implants), artificial organ or a component thereof (e.g., heart valve, ventricular assist devices, total artificial hearts, cochlear implant, visual prosthetic, and components thereof), dental tool, dental implant (e.g., root form, plate form, and subperiosteal implants), biosensor (e.g., glucose and insulin monitor, blood oxygen sensor, hemoglobin sensor, biological microelectromechanical devices (bioMEMs), sepsis diagnostic sensor, and other protein and enzyme sensors), bioelectrode, endoscope (hysteroscope, cystoscope, amnioscope, laparoscope, gastroscope, mediastinoscope, bronchoscope, esophagoscope, rhinoscope, arthroscope, proctoscope, colonoscope, nephroscope, angioscope, thoracoscope, esophagoscope, laryngoscope, and encephaloscope), extracorporeal membrane oxygenation machines, heart-lung machines, surgical applications (e.g., sutures and vascular grafts), vascular applications (e.g., shunts), surgical patches (e.g., hernia patches), and combinations thereof.

In one embodiment, surfaces modified according to the present disclosure can repel a fluid without causing surface adhesion, surface-mediated clot formation, coagulation or aggregation. Non-limiting examples of biological fluids include water, whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, synthetic fluid (e.g., synthetic blood, hormones, nutrients), and combinations thereof.

In another embodiment, surfaces modified according to the present disclosure can repel various types of bacteria. In one embodiment, the type of bacteria repelled by these surfaces is gram positive bacteria. In another embodiment, the type of bacteria repelled by the disclosed modified surfaces is a gram negative bacterium. Non-limiting examples of bacteria repelled by surfaces modified in accordance with the present disclosure include members of the genus selected from the group consisting of *Actinobacillus* (e.g., *Actinobacillus actinomycetemcomitans*), *Acinetobacter* (e.g., *Acinetobacter baumannii*), *Aeromonas*, *Bacillus* (e.g. *Bacillus subtilis*, *Bacillus thuringiensis*), *Bordetella* (e.g., *Bordetella pertussis*, *Bordetella bronchiseptica*, and *Bordetella parapertussis*), *Brevibacillus*, *Brucella*, *Bacteroides* (e.g., *Bacteroides fragilis*), *Burkholderia* (e.g., *Burkholderia cepacia* and *Burkholderia pseudomallei*), *Borelia* (e.g., *Borelia burgdorfen*), *Bacillus* (e.g., *Bacillus anthracis* and *Bacillus subtilis*), *Campylobacter* (e.g., *Campylobacter jejuni*), *Capnocytophaga*, *Cardiobacterium* (e.g., *Cardiobacterium hominis*), *Citrobacter*, *Clostridium* (e.g., *Clostridium tetani*, *Clostridium perfringens*, *Clostridium difficile*), *Chlamydia* (e.g., *Chlamydia trachomatis*, *Chlamydia pneumoniae*, and *Chlamydia psiffaci*), *Eikenella* (e.g., *Eikenella corrodens*), *Enterobacter*, *Enterococcus* (e.g. *Enterococcus faecalis*, *Enterococcus facium*, *Enterococcus gallinarum*), *Escherichia* (e.g., *Escherichia coli*), *Francisella* (e.g., *Francisella tularensis*), *Fusobacterium*, *Flavobacterium*, *Haemophilus* (e.g., *Haemophilus ducreyi* or *Haemophilus influenzae*), *Helicobacter* (e.g., *Helicobacter pylori*), *Kingella* (e.g., *Kingella kingae*), *Klebsiella* (e.g., *Klebsiella pneumonia*, *Klebsiella oxytoca*), *Lactobacillus* sp., *Legionella* (e.g., *Legionella pneumophila*), *Listeria* (e.g., *Listeria monocytogenes*), *Leptospirae*, *Moraxella* (e.g., *Moraxella catarrhalis*), *Morganella*, *Mycoplasma* (e.g., *Mycoplasma hominis* and *Mycoplasma pneumoniae*), *Mycobacterium* (e.g., *Mycobacterium tuberculosis*, *Mycobacterium avium*, *Mycobacterium leprae*), *Neisseria* (e.g., *Neisseria gonorrhoeae* or *Neisseria meningitidis*), *Nocardia farcinica*, *Pasteurella* (e.g., *Pasteurella multocida*), *Proteus* (e.g., *Proteus vulgaris* and *Proteus mirabilis*), *Prevotella*, *Plesiomonas* (e.g., *Plesiomonas shigelloides*), *Pseudomonas* (e.g., *Pseudomonas aeruginosa*), *Providencia*, *Rickettsia* (e.g., *Rickettsia rickettsii* and *Rickettsia typhi*), *Salmonella* (e.g. *Salmonella enterica* sv typhi/paratyphi/typhimurium/enteritidis), *Serratia marcescens*, *Shigella flexneri*, *Stenotrophomonas* (e.g., *Stenotrophomonas maltophila*), *Staphylococcus* (e.g., *Staphylococcus aureus* and *Staphylococcus epidermidis*), *Streptococcus* (e.g., *Streptococcus viridans*, *Streptococcus pyogenes* (group A), *Streptococcus agalactiae* (group B), *Streptococcus bovis*, and *Streptococcus pneumoniae*), *Streptomyces* (e.g., *Streptomyces hygroscopicus*), *Salmonella* (e.g., *Salmonella enteriditis*, *Salmonella typhi*, and *Salmonella typhimurium*), *Serratia* (e.g., *Serratia marcescens*), *Shigella*, *Spirillum* (e.g., *Spirillum minus*), *Treponema* (e.g., *Treponema pallidum*), *Veillonella*, *Vibrio* (e.g., *Vibrio cholerae*, *Vibrio parahaemolyticus*, and *Vibrio vulnificus*), *Yersinia* (e.g., *Yersinia enterocolitica*, *Yersinia pestis*, and *Yersinia pseudotuberculosis*), *Xanthomonas* (e.g., *Xanthomonas maltophilia*) and combinations thereof.

Surfaces modified according to the present disclosure can repel various types of fungi. Non-limiting examples of fungi repelled by modified surfaces include members of the genus *Aspergillus* (e.g., *Aspergillus flavus*, *Aspergillus fumigatus*, *Aspergillus glaucus*, *Aspergillus nidulans*, *Aspergillus niger*, and *Aspergillus terreus*), *Blastomyces dermatitidis*, *Candida* (e.g., *Candida albicans*, *Candida glabrata*, *Candida tropicalis*, *Candida parapsilosis*, *Candida krusei*, and *Candida guillermondii*), *Coccidioides immitis*, *Cryptococcus* (e.g., *Cryptococcus neoformans*, *Cryptococcus albidus*, and *Cryptococcus laurentii*), *Fusarium*, *Histoplasma capsulatum* var. *capsulatum*, *Histoplasma capsulatum* var. *duboisii*, *Mucor* spp. *Paracoccidioides brasiliensis*, *Pneumocystis*, *Sporothrix schenckii*, *Absidia corymbifera*; *Rhizomucor pusillus*, *Rhizopus arrhizous*, and combinations thereof.

Surfaces modified according to the present disclosure can also repel various types of viruses and virus-like particles. In one or more embodiments, the virus repelled by these surfaces is selected from the group consisting of dsDNA viruses, ssDNA viruses, dsRNA viruses, (+)ssRNA viruses, (−)ssRNA viruses, ssRNA-RT viruses, dsDNA-RT viruses, and combinations thereof. Non-limiting examples of viruses repelled by surfaces modified in accordance with the present disclosure include cytomegalovirus (CMV), dengue, Epstein-Barr, Hantavirus, human T-cell lymphotropic virus (HTLV I/II), Parvovirus, hepatitides (e.g., hepatitis A, hepatitis B, and hepatitis C), human papillomavirus (HPV), human immunodeficiency virus (HIV), acquired immunodeficiency syndrome (AIDS), respiratory syncytial virus (RSV), Varicella zoster, West Nile, herpes, polio, smallpox, yellow fever, rhinovirus, coronavirus, Orthomyxoviridae (influenza viruses) (e.g., Influenzavirus A, Influenzavirus B, Influenzavirus C, Isavirus and Thogotovirus), and combinations thereof.

In still another embodiment, surfaces modified according to the present disclosure are capable of repelling particles in suspension or solution without causing surface adhesion, surface-mediated clot formation, coagulation, fouling, or aggregation. The omniphobic nature of the disclosed modified surfaces allows them to protect materials from a wide range of contaminants. Non-limiting examples of particles in suspension or solution include cells (e.g., normal cells, diseased cells, parasitized cells, cancer cells, foreign cells, stem cells, and infected cells), microorganisms (e.g., viruses, virus-like particles, bacteria, bacteriophages), proteins and cellular components (e.g., cell organelles, cell fragments, cell membranes, cell membrane fragments, viruses, virus-like particles, bacteriophage, cytosolic proteins, secreted proteins, signaling molecules, embedded proteins, nucleic acid/protein complexes, nucleic acid precipitants, chromosomes, nuclei, mitochondria, chloroplasts, flagella, biominerals, protein complexes, and minicells).

In yet another embodiment, commercially available devices (e.g., medical-grade apparatus or components) can be treated according to certain aspects of the present disclosure. For example, medical-grade PVC tubes can be treated so that their inner surfaces can possess certain repellant characteristics described in the present disclosure. In one or more embodiments, the surfaces are treated to reduce clotting in blood flowing through the medical tubing.

In some situations, the surfaces can be sterilized before or after the treatment. The ultra slippery coatings as described herein have been demonstrated to be sufficiently robust that they can maintain their slip characteristics, even after sterilization. The surface treatment (e.g., silanization) can be stable or robust enough that the surface maintains its repellant characteristics after an extended period of time (e.g., a day, week, a month, a year or more) and/or with sterilization process.

EXAMPLES

The following examples are presented for the purpose of illustration only and are not intended to be limiting.

Acrylic (PMMA) sheets were plasma treated for 2 minutes at 200 W in 170 mTorr oxygen gas (PlasmaEtch) before silanization.

5% v/v PFC silane (tridecafluorotetrahydrooctyltrichlorosilane, Gelest) was deposited using various different perfluorocarbon (PFC) liquids and different crosslinking agents.

Example 1

Figure 5A:
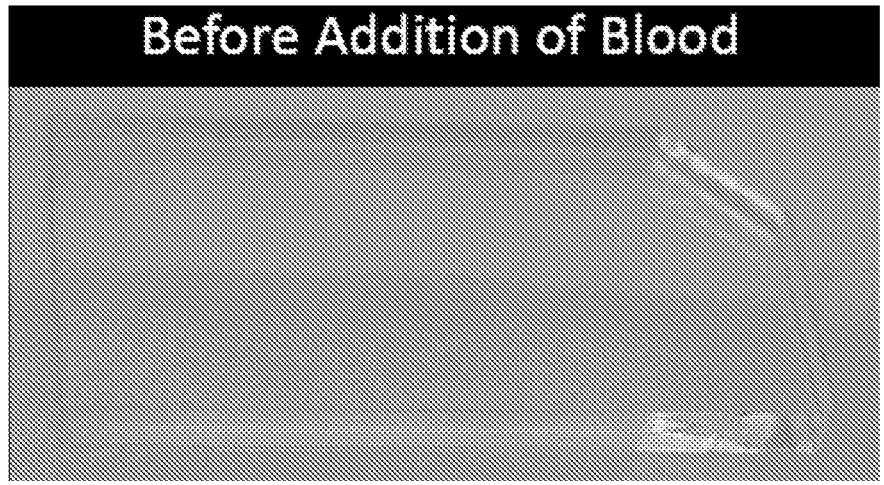
FIGS. 5A-5B is a polymethyl methacrylate (PMMA) substrate coated with perfluorodecalin oil that retains blood even after tilting 90 degrees.
Figure 5B:
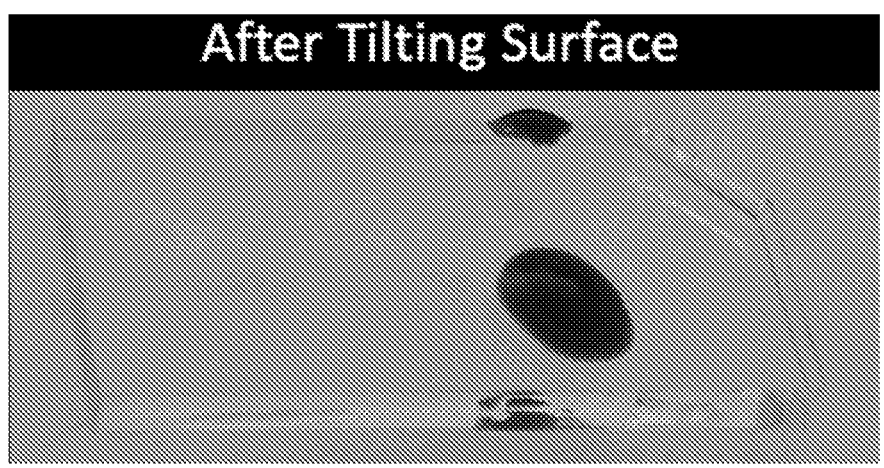

A control sample example was carried out on an unmodified acrylic where untreated PMMA sheet was coated with 15 microliters of high purity perfluorodecalin oil, placed 12-well polystyrene plate and rocked over 2-20 hours at room temperature. Thereafter, 10 microliters of whole human blood anticoagulated with 3.2% sodium citrate was added and the surface was tilted 90 degrees. As shown in FIGS. 5A-5B, blood remained on the surface even after tilting.

Example 2

Figure 6A:
FIGS. 6A-6B, 7A-7B, 8A-8B, and 9A-9B are images of different polymethyl methacrylate (PMMA) substrate coated with an ultra-slippery surface having anchoring molecules crosslinked with different crosslinking agents and perfluorodecalin as the lubricating liquid, where blood easily slides away after tilting in accordance with certain embodiments.
Figure 6B:
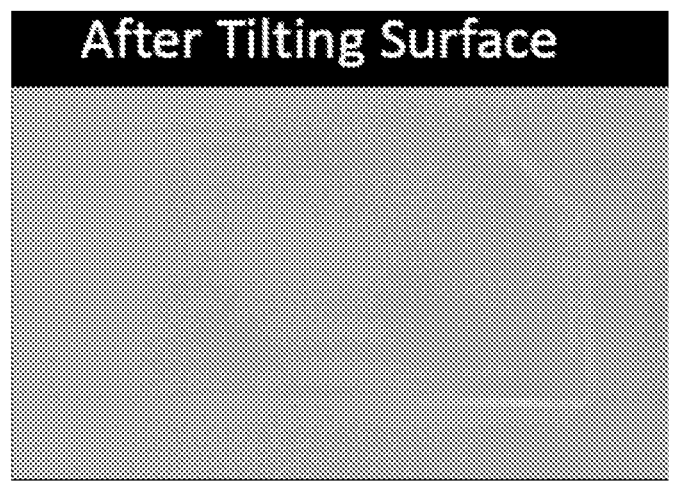

In this example, the same test as described in Example 1 was carried out, except perfluorodecalin (PFD) (Fluoromed, APF-140HP) was used as the PFC oil and 50 microliters of perfluoronyl dimethicone (Pecosil FSL-300, Phoenix Chemical) was used as the crosslinking agent. Moreover, surfaces were rinsed with PFD to remove any unreacted silane or diol, and then blown dry with nitrogen. They were then baked at 60° C. under vacuum for 2-6 hours. This removed all PFD in the gel network and ensured complete reaction of the trichlorosilane. Similar blood application and tilting testing as described in Example 1 was carried out and, as shown in FIGS. 6A-6B, blood was completely repelled.

Example 3

Figure 7A:
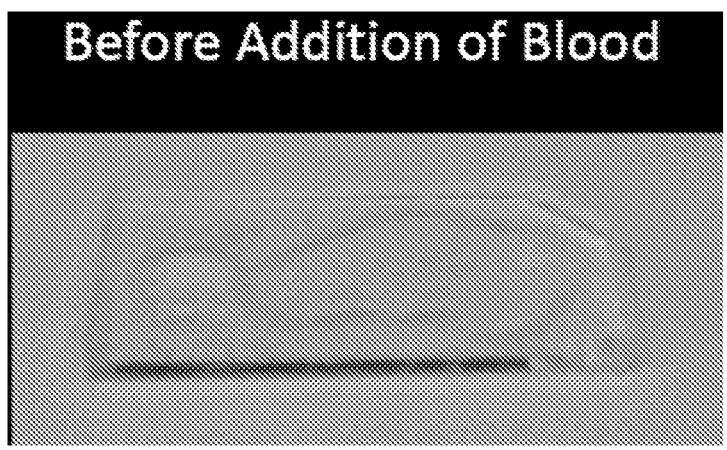
Figure 7B:
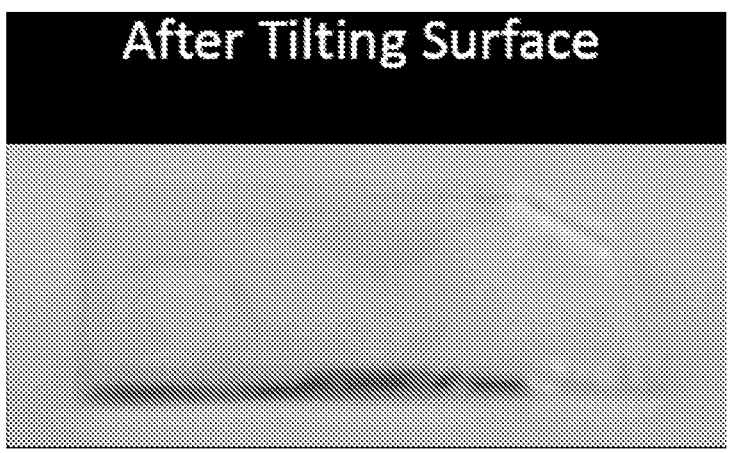

In this example, the same test as described in Example 2 was carried out, except perfluorodecalin (PFD) (Fluoromed, APF-140HP) was used as the PFC oil and 50 microliters of polydimethylsiloxane (PDMS) hydroxyl-terminated, average molecular weight of 550 (Sigma, 481939), was used as the crosslinking agent. Similar blood application and tilting testing was carried out and, as shown in FIGS. 7A-7B, blood was completely repelled.

Example 4

Figure 8A:
Figure 8B:

In this example, the same test as described in Example 2 was carried out, except perfluorodecalin (PFD) (Fluoromed, APF-140HP) was used as the PFC oil and 50 microliters of polyethylene glycol (PEG) MW 8000 (Affymetrix), was used as the crosslinking agent. Similar blood application and tilting testing was carried out and, as shown in FIGS. 8A-8B, blood was completely repelled.

Example 5

Figure 9A:
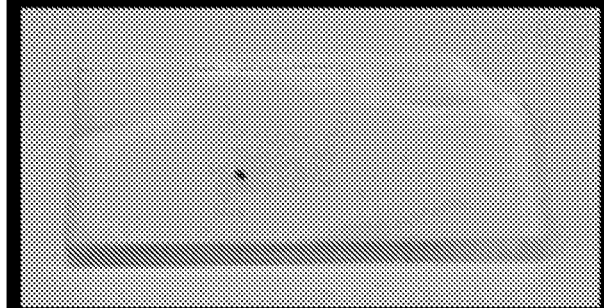
Figure 9B:
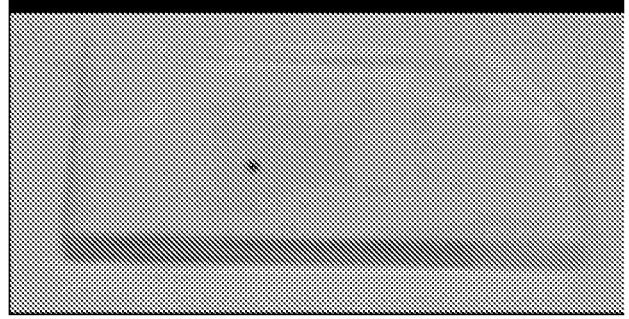

In this example, the same test as described in Example 2 was carried out, except perfluorodecalin (PFD) (Fluoromed, APF-140HP) was used as the PFC oil and 50 microliters of perfluoroglutaric acid (PFGA), (Sigma, 196908-5G), was used as the crosslinking agent. Similar blood application and tilting testing was carried out and, as shown in FIGS. 9A-9B, blood was completely repelled.

Example 6

In this example, the same test as described in Example 2 was carried out, except perfluorodecalin (PFD) (Fluoromed, APF-140HP) was used as the PFC oil and 50 microliters of PFC silane, (Gelest), was used as the crosslinking agent. Similar blood application and tilting testing was carried out and blood was completely repelled.

Example 7

Figure 10:
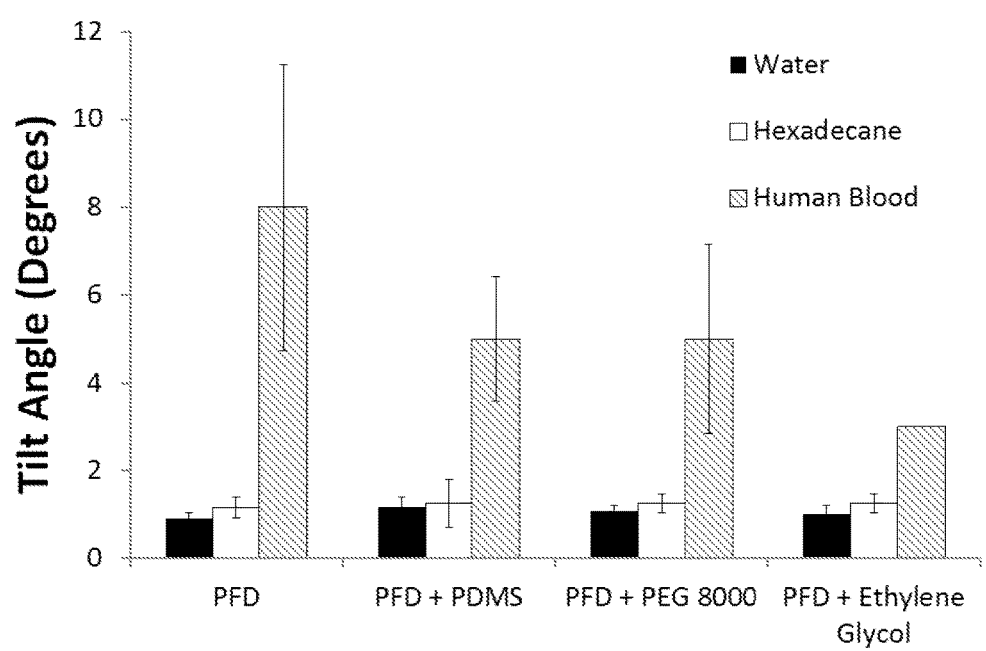
FIG. 10 shows the tilting angle that is needed to slide away various repellent liquids with and without an ultra-slippery surfaces in accordance with certain embodiments.

The angle at which the different fluids slide away from the surfaces described in Examples 3, 4 and 6 were compared. Moreover, surfaces crosslinked using ethylene glycol as the crosslinking agent was also studied. As shown in FIG. 10, while all surfaces easily repelled water and hexadecane as evidenced by sliding off at about 1 degree tilt angle, citrated human blood slid off the surfaces having crosslinked network (PFD+PDMS; PFD+PEG8000, and PFD+Ethylene Glycol) much more easily.

Example 8

Silicone tubing was impregnated with silicone oil as the lubricating liquid to repel an immiscible fluid, in this case, blood. The tubing swelled significantly, changing its physical dimensions and lost its mechanical compliance and elasticity, rendering the tubing and lubricating layer susceptible to mechanical degradation.

As will be apparent to one of ordinary skill in the art from a reading of this disclosure, aspects of the present disclosure can be embodied in forms other than those specifically disclosed above. For example, a desired functionality, intended to achieve certain medically relevant response (such as anti-clotting, blood or other biological fluid repelling, drug releasing, infection-suppressing, tissue growth promoting, etc.), can be engineered into the composition of the anchoring and lubricating layers. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

What is claimed is:

1. An article having a slippery surface, comprising:
   a substrate comprising an anchoring layer, the anchoring layer comprising:
      anchoring molecules comprising a head group attached to the substrate and a functional tail group directly or indirectly attached to the head group; and
      a crosslinking agent that crosslinks the anchoring molecules to one another;
   a lubricating layer comprising a lubricating liquid having an affinity for the functional tail group and disposed over the anchoring layer, wherein the anchoring layer and the lubricating layer are held together by non-covalent attractive forces,
   wherein the anchoring layer and the lubricating layer form a slippery surface configured and arranged for contact with a material that is substantially immiscible with the lubricating liquid,
   wherein the slippery surface is omniphobic, and
   wherein the article is substantially free of anchoring molecules not bound to the substrate, unreacted crosslinking agent, and reaction byproducts between the anchoring molecules and the crosslinking agent.

2. The article of claim 1, wherein the immiscible material is selected from the group consisting of a liquid, complex fluid, solution, suspension, a gas and a solid.

3. The article of claim 1, wherein said head group of the anchoring molecules include ethers, silyl ethers, siloxanes, esters of carboxylic acids, esters of sulfonic acids, esters of sulfinic acids, esters of sulfuric acids, esters of phosphonic acids, esters of phosphinic acids, esters of phosphoric acids, silyl esters of carboxylic acids, silyl esters of sulfonic acids, silyl esters of sulfinic acids, silyl esters of sulfuric acids, silyl esters of phosphonic acids, silyl esters of phosphinic acids, silyl esters of phosphoric acids, oxides, sulfides, carbocycles, heterocycles with at least one oxygen atom, heterocycles with at least one nitrogen atom, heterocycles with at least one sulfur atom, heterocycles with at least one silicon atom, 'click' reactions-derived heterocycles, Diels-Alder reactions-derived carbocycles, Diels-Alder reactions-derived heterocycles, amides, imides, sulfides, thiolates, metal thiolates, urethanes, oximes, hydrazides, hydrazones, or combinations thereof.

4. The article of claim 1, wherein the functional tail group of the anchoring molecules comprise a fluorocarbons or perfluorocarbons, and the lubricating layer comprises hydrocarbon liquid, fluorinated organic liquid, or perfluorinated organic liquid.

5. The article of claim 1, wherein the functional tail group of the anchoring molecules includes perfluorocarbons, perfluorooligoethers or perfluoropolyethers.

6. The article of claim 1, wherein, the anchoring molecules comprise a silyl group covalently attached to a perfluorocarbon tail, and the lubricating layer comprises fluorinated organic liquid, or perfluorinated organic liquid.

7. The article of claim 1, wherein, the anchoring molecules comprise a phosphonate or carboxylate group covalently attached to a perfluorocarbon tail, and the lubricating layer comprises fluorinated organic liquid, or perfluorinated organic liquid.

8. The article of claim 1, wherein the slippery surface is slippery to water-based and hydrocarbon-based liquids.

9. The article of claim 1, wherein the slippery surface is slippery to biological fluids.

10. The article of claim 1, wherein the slippery surface is slippery to non-heparinized blood.

11. The article of claim 1, wherein the slippery surface comprises beads, hollow fibers, membranes, thin films, tubing, fluidized bed, filters, mixers, impellers, connectors, cannula, flow cells, or needles.

12. The article of claim 1, wherein the surface comprises medical grade materials or medical devices.

13. A method of preventing adhesion, adsorption, surface-mediated clot formation, or coagulation of a material onto a substrate, comprising
   providing a slippery surface comprising an anchoring layer, the anchoring layer comprising anchoring molecules having a head group attached to a substrate and a functional tail group directly or indirectly attached to the head group and crosslinking agents that crosslink the anchoring molecules to one another; and a lubricating layer comprising a lubricating liquid having an affinity for the functional tail group and disposed over the anchoring layer, wherein the slippery surface is omniphobic and substantially free of anchoring molecules not bound to the substrate, unreacted crosslinking agent, and reaction byproducts between the anchoring molecules and the crosslinking agent, and wherein the anchoring layer and the lubricating layer are held together by non-covalent attractive forces; and
   contacting a material that is immiscible with the lubricating layer to the slippery surface.

14. The method of claim 13, wherein the head group is covalently attached to the surface.

15. The method of claim 13, wherein the anchoring layer forms a monomolecular layer on the surface.

16. The method of claim 13, wherein the surface is selected from the group consisting of acrylic, glass, polymers, metals, carbon, plastics, paper, ceramics, and combinations thereof.

17. The method of claim 13, wherein the surface is treated to activate the surface prior to exposure to the anchoring layer.

18. The method of claim 17, wherein activation comprises acid treatment, base treatment, oxidization, ammonization, heat, peroxide, photon, electron, ion, plasma, or microwave treatment.

19. The method of claim 13, wherein the functional tail group is a perfluorocarbon.

20. The method of claim 13, wherein the functional tail group is a fluorocarbon.

21. The method of claim 13, wherein the immiscible material is selected from the group consisting of non-viscous and viscous liquids, complex fluids, semi-solids, tacky liquids, solids and combinations thereof.

22. The method of claim 13, wherein the surface reduces coagulation of blood.

23. The method of claim 13, wherein the surface reduces adhesion of fibrin, fibrinogen, blood proteins, platelets, leukocytes, red blood cells and/or coagulation factors.

24. The method of claim 13, wherein the immiscible material contains an additive, the additive being selected from the group consisting of a solute, a particulate, an emulsion, a liposome, a bubble, a droplet, or a combination thereof.

25. The method of claim 24, wherein the immiscible material is repelled by the surface and the additive is attracted to the surface.

26. The method of claim 24, wherein the immiscible material and the additive are repelled by the surface.

27. The method of claim 13, wherein the lubricating layer, the anchoring layer, the substrate or combinations thereof contains an additive selected from the group consisting of a solute, a particulate, an emulsion, a liposome, a bubble, a droplet, or a combination thereof.

28. The method of claim 27, wherein the additive is eluted from the lubricating layer, the anchoring layer, the substrate, or combination thereof into the immiscible material.

29. The method of claim 13, wherein the immiscible material is selected from the group consisting of whole blood, plasma, serum, buffy coat, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, and combinations thereof.

30. The method of claim 13, wherein the immiscible material is a solution or suspension containing bacteria selected from the group consisting of *Actinobacillus, Acinetobacter* (e.g., *Acinetobacter baumannii*), *Aeromonas, Bordetella, Brevibacillus, Brucella, Bacteroides, Burkholderia, Borelia, Bacillus, Campylobacter, Capnocytophaga, Cardiobacterium, Citrobacter, Clostridium, Chlamydia, Eikenella, Enterobacter, Escherichia, Francisella, Fusobacterium, Flavobacterium, Haemophilus, Helicobacter, Kingella, Klebsiella, Legionella, Listeria, Leptospirae, Moraxella, Morganella, Mycoplasma, Mycobacterium, Neisseria, Pasteurella, Proteus, Prevotella, Plesiomonas, Pseudomonas, Providencia, Rickettsia , Stenotrophomonas, Staphylococcus, Streptococcus* (group A), *Streptococcus agalactiae* (group B), *Streptococcus bovis, Streptococcus pneumoniae, Streptomyces, Salmonella, Serratia, Shigella, Spirillum, Treponema, Veillonella, Vibrio, Yersinia, Xanthomonas,* and combinations thereof.

31. The method of claim 13, wherein the immiscible material is a solution or suspension containing fungi selected from the group consisting of a member of the genus *Aspergillus, Blastomyces dermatitidis, Candida, Coccidioides immitis, Cryptococcus, Histoplasma capsulatum* var. *capsulatum, Histoplasma capsulatum* var. *duboisii, Paracoccidioides brasiliensis, Sporothrix schenckii, Absidia corymbifera; Rhizomucor pusillus, Rhizopus arrhizous,* and combinations thereof.

32. The method of claim 13, wherein the material is a solution or suspension containing viruses selected from the group consisting of cytomegalovirus (CMV), dengue, Epstein-Barr, Hantavirus, human T-cell lymphotropic virus (HTLV I/II), Parvovirus, hepatitides, human papillomavirus (HPV), human immunodeficiency virus (HIV), acquired immunodeficiency syndrome (AIDS), respiratory syncytial virus (RSV), Varicella zoster, West Nile, herpes, polio, smallpox, yellow fever, rhinovirus, coronavirus, Orthomyxoviridae (influenza viruses), and combinations thereof.

33. The method of claim 13, wherein the material is a solution or suspension containing particles selected from the group consisting of normal cells, diseased cells, parasitized cells, cancer cells, foreign cells, stem cells, and infected cells, microorganisms, viruses, virus-like particles, bacteria, bacteriophages, proteins, cellular components, biofilm, biofilm components, cell organelles, cell fragments, cell membranes, cell membrane fragments, cytosolic proteins, secreted proteins, signaling molecules, embedded proteins, nucleic acid/protein complexes, nucleic acid precipitants, chromosomes, nuclei, mitochondria, liposomes, vesicles, chloroplasts, flagella, biominerals, protein complexes, and minicells.

34. A method of making an article having a slippery surface, comprising:
contacting a substrate with anchoring molecules having a head group that is reactive with the substrate and a functional tail group directly or indirectly attached to the head group to form an anchoring layer on the substrate;
crosslinking the anchoring molecules to one another using a crosslinking agent;
washing away anchoring molecules not bound to the substrate, unreacted crosslinking agent, and reaction byproducts between the anchoring molecules and the crosslinking agent; and
contacting the anchoring layer with a lubricating liquid having an affinity for the functional tail group to form a lubricating layer disposed over the anchoring layer, wherein the anchoring layer and the lubricating layer are held together by non-covalent attractive forces,
wherein the anchoring layer and the lubricating layer form a slippery surface configured and arranged for contact with a material that is immiscible with the lubricating liquid, and wherein the slippery surface is omniphobic.

35. The method of claim 34, wherein contacting the anchoring layer with lubricating liquid comprises passing lubricating liquid through micropassages or nanopassages in the substrate.

36. The method of claim 34, wherein the substrate comprises a reservoir through which lubricating liquid is replenished.

37. The method of claim 34, wherein the substrate comprises tubing and wherein contacting the anchoring layer with lubricating liquid comprises passing boluses of lubricating liquid through the tube.

38. The method of claim 34, wherein the lubricating liquid is replenished on the anchoring layer.

39. The article of claim 1, wherein the article is selected from the group consisting of: cannula, catheter, central line, peripherally inserted central catheter (PICC) line, urinary cathether, vascular cathether, peritoneal dialysis catheter, central venous catheters, catheter connector, shunt, capillary tube, endotracheal tube, tubing connector, defibrillator, biosensor, endoscope, extracorporeal membrane oxygenation machines, heart-lung machines, suture and vascular grafts, vascular shunts, and combinations thereof.

40. The method of claim 13, wherein the surface is a surface of an article selected from the group consisting of: cannula, catheter, central line, peripherally inserted central catheter (PICC) line, urinary cathether, vascular cathether, peritoneal dialysis catheter, central venous catheters, catheter connector, shunt, capillary tube, endotracheal tube, tubing connector, defibrillator, biosensor, endoscope, extracorporeal membrane oxygenation machines, heart-lung machines, suture and vascular grafts, vascular shunts, and combinations thereof.

41. The article of claim 1, the lubricating layer comprises a fluorinated hydrocarbon liquid or a perfluorocarbon liquid.

* * * * *